United States Patent
Driehuys et al.

(10) Patent No.: US 7,867,477 B2
(45) Date of Patent: *Jan. 11, 2011

(54) METHODS FOR IN VIVO EVALUATION OF PULMONARY PHYSIOLOGY AND/OR FUNCTION USING NMR SIGNALS OF POLARIZED $^{129}$XE

(75) Inventors: Bastiaan Driehuys, Durham, NC (US); Margaret Hall, Little Kingshill (GB); Claudio Marelli, Amersham (GB); Sven Mansoon, Bjarred (SE); Jan Wolber, Malmo (SE)

(73) Assignee: Medi-Physics Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/623,352

(22) Filed: Jan. 16, 2007

(65) Prior Publication Data

US 2007/0110669 A1     May 17, 2007

Related U.S. Application Data

(60) Division of application No. 10/356,240, filed on Jan. 31, 2003, now Pat. No. 7,179,450, which is a continuation-in-part of application No. 10/236,233, filed on Sep. 6, 2002, now abandoned.

(60) Provisional application No. 60/323,667, filed on Sep. 20, 2001.

(51) Int. Cl.
A61B 5/055     (2006.01)
(52) U.S. Cl. .................. 424/9.3; 424/1.11; 424/9.1; 534/7
(58) Field of Classification Search .............. 424/1.11, 424/9.1, 9.2, 9.3, 9.32, 9.36; 534/7; 600/410, 600/420; 436/173
See application file for complete search history.

(56) References Cited

U.S. PATENT DOCUMENTS

| | | | |
|---|---|---|---|
| 4,793,357 A | 12/1988 | Lindstrom | |
| 5,190,744 A | 3/1993 | Rocklage et al. | |
| 5,509,412 A | 4/1996 | Bahn | |
| 5,545,396 A | 8/1996 | Albert et al. | 424/93 |
| 5,572,126 A | 11/1996 | Shinnar | |
| 5,617,859 A | 4/1997 | Souza et al. | 128/653.2 |
| 5,617,860 A | 4/1997 | Chupp et al. | 128/653.4 |
| 5,642,625 A | 7/1997 | Cates, Jr. et al. | 62/55.5 |
| 5,809,801 A | 9/1998 | Cates, Jr. et al. | 62/637 |
| 5,811,076 A | 9/1998 | Brasch et al. | 424/9.363 |
| 5,936,404 A | 8/1999 | Ladebeck et al. | 324/300 |
| 6,033,645 A | 3/2000 | Unger et al. | 424/9.5 |
| 6,051,208 A | 4/2000 | Johnson et al. | 424/9.3 |
| 6,079,213 A | 6/2000 | Driehuys et al. | 62/3.1 |
| 6,158,434 A | 12/2000 | Lugtigheid et al. | |
| 6,237,363 B1 | 5/2001 | Zollinger et al. | 62/600 |
| 6,338,836 B1 | 1/2002 | Kuth et al. | 424/9.3 |
| 6,346,229 B1 * | 2/2002 | Driehuys et al. | 424/9.36 |
| 6,370,415 B1 | 4/2002 | Weiler et al. | 600/410 |
| 6,491,895 B2 * | 12/2002 | Driehuys et al. | 424/9.36 |
| 6,630,126 B2 * | 10/2003 | Driehuys et al. | 424/9.3 |
| 6,696,040 B2 * | 2/2004 | Driehuys | 424/9.3 |
| 6,808,699 B2 * | 10/2004 | Driehuys et al. | 424/9.36 |
| 6,991,777 B2 * | 1/2006 | Driehuys et al. | 424/9.1 |
| 7,179,450 B2 * | 2/2007 | Driehuys et al. | 424/9.36 |
| 7,357,917 B2 * | 4/2008 | Driehuys | 424/9.3 |
| 2001/0041834 A1 | 11/2001 | Mugler et al. | |
| 2002/0006382 A1 | 1/2002 | Driehuys et al. | |
| 2002/0043267 A1 | 4/2002 | Weiler et al. | |

FOREIGN PATENT DOCUMENTS

| | | |
|---|---|---|
| EP | 0933062 A | 4/1999 |
| GB | 2091884 | 4/1982 |
| WO | WO97/37239 | 10/1997 |
| WO | WO99/07415 | 2/1999 |
| WO | WO99/25243 | 5/1999 |
| WO | WO99/47940 | 9/1999 |
| WO | WO99/52428 | 10/1999 |
| WO | WO99/53332 | 10/1999 |
| WO | WO00/23797 | 4/2000 |
| WO | WO00/40972 | 7/2000 |

(Continued)

OTHER PUBLICATIONS

Albert et al., "Susceptibility Changes Following Bolus Injections", Appendix B reprint from Magnetic Resonance in Medicine 29 700-708 (1993).

(Continued)

Primary Examiner—D L Jones
(74) Attorney, Agent, or Firm—Robert F. Chisholm

(57) ABSTRACT

In certain embodiments, methods of the present invention obtain dynamic data sets of an NMR spectroscopy signal of polarized $^{129}$Xe in a selected structure, environment, or system. The signal data can be used to evaluate: (a) the physiology of a membrane or tissue; (b) the operational condition or function of a body system or portion thereof (when at rest or under stimulation); and/or (c) the efficacy of a therapeutic treatment used to treat a diagnosed disorder, disease, or condition. Thus, the present invention provides methods for screening and/or diagnosing a respiratory, cardiopulmonary disorder or disease such as chronic heart failure, and/or methods for monitoring the efficacy of therapeutics administered to subject to treat the disorder or disease.

27 Claims, 15 Drawing Sheets

FOREIGN PATENT DOCUMENTS

| WO | WO01/74246 | 10/2001 |
|---|---|---|
| WO | WO02/04709 | 1/2002 |

OTHER PUBLICATIONS

Albert et al., "Measurement of $^{129}$Xe T1 in Blood to Explore the Feasibility of Hyperpolarized $^{129}$Xe MRI," Jour. Comp. Ass. Tomography, vol. 19, No. 6 (Nov.-Dec. 1995).

Albert et al., "$^{129}$Xe Relaxation Catalysis by Oxygen", Abstracts of the 11th Annual Meetings of the Society for Magnetic Resonance Medicine, Abstract No. 4710 (1992).

Bachert et al., *Nuclear Magnetic Resonance Imaging of Airways in Humans with Use of Hyperpolarized $^3$He*, MRM 36, pp. 192-196 (1996).

Bárány, M. et al., "High Resolution Proton Magnetic Resonance Spectroscopy of Human Brain and Liver," Magn. Reson. Imaging, 5:393 (1987).

Belliveau et al., Functional Cerebral Imagining by Susceptibility-Contrast NMR, Dated Dec. 7, 1989; Magnetic Resonance in Medicine 14, 538-546 (1990).

Bifone, et al., "NMR of laser-polarized xenon in human blood," Proc. Natl. Acad. Sci. USA, vol. 93, pp. 12932-12936 (Nov. 1996).

Brookeman, J.R., "MRS and MRI of Hyperpolarized $^{129}$Xe: Studies in Human Volunteers," Proc ISMRM (1998).

Brunner et al., "Communications: Gas Flow MRI Using Circulating Laser-Polarized $^{129}$Xe," J. Mag. Res. vol. 138, pp. 155-159 (1999).

Chen et al., "MR Microscopy of Lung Airways with Hyperpolarized $^3$He," Mag. Reson. In Med., vol. 39, No. 1, pp. 79-84 (Jan. 1998).

Chupp et al., "Chemical Shift Imagining of Laser-Polarized $^{129}$XE Magnetization In Rats in Vivo", European Radiology 9:B45 (1999).

de Lange et al., "Lung Airspaces: MR Imaging evaluation with Hyperpolarized Helium-3 Gas,"Radiology 210, 851-857(1999).

Deningcr et al., "Quantification of Regional Intrapulmonary Oxygen Partial Pressure Evolution during Apnea by $^3$He MRI," J. Mag. Res., vol. 141, pp. 207-216 (1999).

Diehl et al., "Nuclear Magnetic Relaxation of the $^{129}$Xe and $^{131}$Xe Isotopes of Xenon Gas Dissolved in Isotropic and Anisotropic Liquids," J. Magn. Reson., vol. 88, pp. 660-665 (1990).

Donnelly et al., "Cystic Fibrosis: Combined Hyperpolarized 3He-enhanced and Conventional Proton MR Imaging in the Lung—Preliminary Observations," Radiology 212 (Sep. 1999), 885-889 (1999).

Driehuys et al., "Surface Relaxation Mechanisms of Laser-Polarized $^{129}$Xe", Physical Review Letters vol. 74, No. 24, p. 4943-4946, dated Jun. 12, 1995.

Eberle et al., "Analysis of intrapulmonary $O_2$ concentration by MR imaging of inhaled hyperpolarized helium-3," Am. Physiological Soc., pp. 2043-2052 (1999).

Eberle et al., "Determination of Regional Intrapulmonary Oxygen Concentration by Magnetic Resonance Imaging of inhaled Hyperpolarized $^3$Helium," Anesthesiology, vol. 89, No. 3A (Sep. 1998).

Gao et al., "Magnetization and Diffusion Effects in NMR Imaging of Hyperpolarized Substances", MRM 37:153-158 (1997).

Goodson et al., "In vivo NMR and MRI Using Injection Delivery of Laser-Polarized Xenon," 94 Proc. Natl. Acad. Sci. USA, pp. 14725-14729 (1997).

Gregory et al., "Pore Structure Determinations of Silica Aerogels by $^{129}$Xe NMR Spectroscopy and Imaging," J. Mag. Reson., vol. 131, No. 2, pp. 327-335 (Apr. 1998).

Grover, B.D., "Noble-Gas NMR Detection through Noble-Gas-Rubidium Hyperfine Contact Interaction," Phys. Rev. Lett., vol. 40, No. 6, pp. 391-392 (1978).

Hedlund, L. W., M.D. Shattuck, and G.A.Johnson. "Three-dimensional MR microscopy of pulmonary dynamics" in 1996. New York, NY: Society of Magnetic Resonance.

Hou, et al., "Optimization of Fast Acquisition Methods for Whole-Brain Relative Cerebral Blood Volume (rCBV) Mapping with Susceptibility Contrast Agents," J. Mag. Res. Imaging, vol. 9 pp. 233-239 (1999).

Il'yasov et al., "129Xe NMR in Study of Tissues and Plants," Appl. Magn. Reson. vol. 17, pp. 17-84, (1999).

Intenrational Search Report and Written Opinionfor PCT/US2004/002782 dated Jun. 25, 2004 dated Jul. 16, 2004.

Jameson et al., "Nuclear Spin Relaxation by Intermolecular Magnetic Dipole Coupling in the Gas Phase. 129Xe in Oxygen," J. Chem. Phys., vol. 89, p. 4074-4081 (1988).

Kaatz et al., "A comparison of molecular hyperpolarizabilities from gas and liquid," J. Chem. Phys., vol. 108, No. 3, pp. 849-856 (Jan. 15, 1998).

Kaiser, et al., "Diffusion and field-gradient effects in NMR Fourier spectroscopy," J. Chem. Phys., vol. 60, No. 8, pp. 2967-2979 (Apr. 15, 1974).

Kauczor et al., "Normal and Abnormal Pulmonary Ventilation: Visualization at Hyperpolarized He-3 MR Imaging[1]," Radiology, vol. 201, No. 2, pp. 564-568 (1996).

Le Bihan, "Magnetic Resonance Imaging of Perfusion*," Mag. Reson. In Med., vol. 14, pp. 283-292 (1990).

Luhmer et al., "Study of Xenon Binding in Cryptophanc-A Using Laser-Induced NMR Polarization Enhancement", J. Am. Chem. Soc. Mar. 30, 1999, 121, 3502-3512.

MacFall et al., "Human Lung Air Spaces: Potential for MR Imaging with Hyperpolarized He-3[1]," Radiology, vol. 200, No. 2, pp. 553-558 (1996).

Mansfeld et al., "The use of $^{129}$Xe NMR exchange spectroscopy for probing the microstructure of porous materials," Chem. Phys. Ltrs., vol. 213, No. 1, 2, pp. 153-157 (Oct. 1, 1993).

Mansson et.al. "Characterization of diffusing capacity and perfusion of the rat lung in a lipopolysaccharide disease model using hyperpolarized 129Xe" Magnetic Resonance in Medicine: Official Journal of the society of Magnetic Resonance in Medicine/society of Magnetic Resonance in Medicine Dec. 2003, vol. 50, No. 6 pp. 1170-1179.

Martin, "The Pharmacokinetics of Hyperpolarized Xenon: Implications for Cerebral MRI," Jour. Magn. Reson. Imag., vol. 7, No. 5, pp. 848-854 (Sep.-Oct. 1997).

Mazitov et al., "NMR Spectroscopy of $^{129}$Xe Dissolved in Tissues of Animals and Plants in vitro: Effect of Tissue with Cancer" Doklady Biophysics vols. 364-366, 1999.

McAdams et al., "Hyperpolarized 3He-Enhanced MR Imaging of Lung Transplant Recipients: Preliminary Results," AJR 173, 955-959 (1999).

Miller et al., "Xenon NMR: Chemical shifts of a general anesthetic common solvents, proteins, and membranes", Proc. of the Nat. Acad. of Sci. (USA), vol. 78, No. 8, pp. 4946-4949 (Aug. 1981).

Miller, "$^{129}$Xe NMR in Polymers," Rubber Chem. And Tech., vol. 66, pp. 455-461 (1993).

Möller et. al., "Magnetic Resonance Angiography with Hyperpolarized 129Xe Dissolved in Lipid Emulsion," 41 Mag. Res. Med. No. 5, pp. 1058-1064 (1999).

Moschos, A. et al., "Communications Nuclear Magnetic Relaxation of Xenon-129 Dissolved in Organic Solvents," J. Mag. Reson., vol. 95, pp. 603-606 (1991).

Mugler, III et al., "MR Imaging and Spectroscopy Using Hyperpolarized 129Xe Gas: Preliminary Human Results," 37 Magn. Reson. In Med., vol. 37, No. 6, pp. 809-815 (1997).

Patyal, "Longitudinal Relaxation and Diffusion Measurements Using Magnetic Resonance Signals from Laser-Hyperpolarized $^{129}$Xe Nuclei," J. Magn. Reson., vol. 126, No. 1, pp. 58-65, May 1997.

Peled et al., "Determinants of Tissue Delivery for $^{129}$Xe Magnetic Resonance in Humans," Mag. Res. Med, vol. 36, pp. 340-343 (1996).

Pennisi, Breathe (xenon) deeply to see lungs clearly, Sci. News, vol. 146, p. 70.

Pfeffer et al., "$^{129}$Xe gas NMR spectroscopy and imaging with a whole-body imager," J. Mag. Reson., Ser. A., vol. 108, No. 1, pp. 106-109 (May 1994).

Pietraβ et al., "Optically Polarized 129Xe in NMR Spectroscopy," Advanced Materials, pp. 826-838 (1995).

Raftery, et al. , "High-Field NMR of Adsorbed Xenon Polarized by Laser Pumping," Phys. Rev. Lett., vol. 66, No. 5, pp. 584-587 (Feb. 4, 1991).

Rosen et al., "Perfusion Imaging by Nuclear Magnetic Resonance," Mag. Reson. Quart., vol. 5, No. 4, pp. 263-281 (1989).

Rosen et al., Polarized $^{129}$Xe optical pumping/spin exchange and delivery system for magnetic resonance spectroscopy and imaging studies, Rev. Sci. Instrum., vol. 70, No. 2, pp. 1546-1552 (Feb. 1999).

Ruppert et al., "NMR of hyperpolarized $^{129}$Xe in the canine chest: spectral dynamics during a breath-hold," NMR Biomed., vol. 13, pp. 220-228 (2000).

Salerno et al. "High-Resolution Volumetric Imaging of the Lung Air Spaces Using Hyperpolarized $^3$He and Spiral-Trajectory Pulse Sequences," Proc. Intl. Soc. Mag. Reson. Med. 9, 1 page (2001).

Salerno et al. "Time-Dependent Hyperpolarized $^3$He Diffusion MR Imaging: Initial Experience in Healthy and Emphysematous Lungs," Proc. Intl. Soc. Mag. Reson. Med. 9, 1 page (2001).

Schoenborn, "Binding of Xenon to Horse Haemoglobin," Nature, vol. 208, pp. 760-762 (Nov. 20, 1965).

Song et al., "Effects of Diffusion on Magnetic Resonance Imaging of Laser-Polarized Xenon Gas," Jour. Chem. Phys., vol. 108, No. 15, pp. 6233-6239 (Apr. 1998).

Swanson et al., "Brain MRI with Laser-Polarized $^{129}$Xe," Mag. Res. Med., vol. 38, pp. 695-698 (1997).

Swanson, et.al. "Distribution and Dyamics of Laser-Polarized 129Xe Magnetization Invivo" Mag. Rs. Med., vol. 42, pp. 1137-1145 (1999).

Tilton, Jr., et al, "Nuclear Magnetic Resonance Studies of Xenon-129 with Myoglobin and Hemoglobin," Biochemistry, vol. 21, No. 26, pp. 6850-6857 (1982).

Tseng et al., "NMR of Laser-Polarized $^{129}$Xe in Blood Foam," J. Mag. Res., vol. 126, pp. 79-86 (1997).

Wagshul, "In Vivo MR Imaging and Spectroscopy Using Hyperpolarized 129Xe," Mag. Reson. Med., vol. 36, No. 2, pp. 183-191 (Aug. 1996).

Wolber et al. "In vivo hyperpolarized $^{129}$Xe spectroscopy in tumors," Proc. Int'l. Mag. Reson. Med. 8, 1440 (2000).

Wolber et al. "In vivo hyperpolarized $^{129}$Xe spectroscopy in tumors," Mag. Reson. Med. 46, pp. 586-591 (2001).

Wolber et al., "Spin-lattice relaxation of laser-polarized xenon in human blood," 96 Proc. Natl. Acad. Sci. USA, pp. 3664-3669 (Mar. 1999).

Wu et al., "Experimental Studies of Wall Interactions of Adsorbed Spin-Polarized $^{131}$Xe Nuclei," Phys. Rev. A, vol. 42, No. 5, pp. 2774-2784 (Sep. 1, 1990).

Yablonskiy et al., "Quantitative in vivo assessment of lung microstructure at the alveolar level with hyperpolarized $^3$He diffusion MRI" www.pnas.org./cgi/doi/10.1073/pnas.052594699, PNAS, Mar. 5, 2002, vol. 99, No. 5, 3111-3116.

* cited by examiner

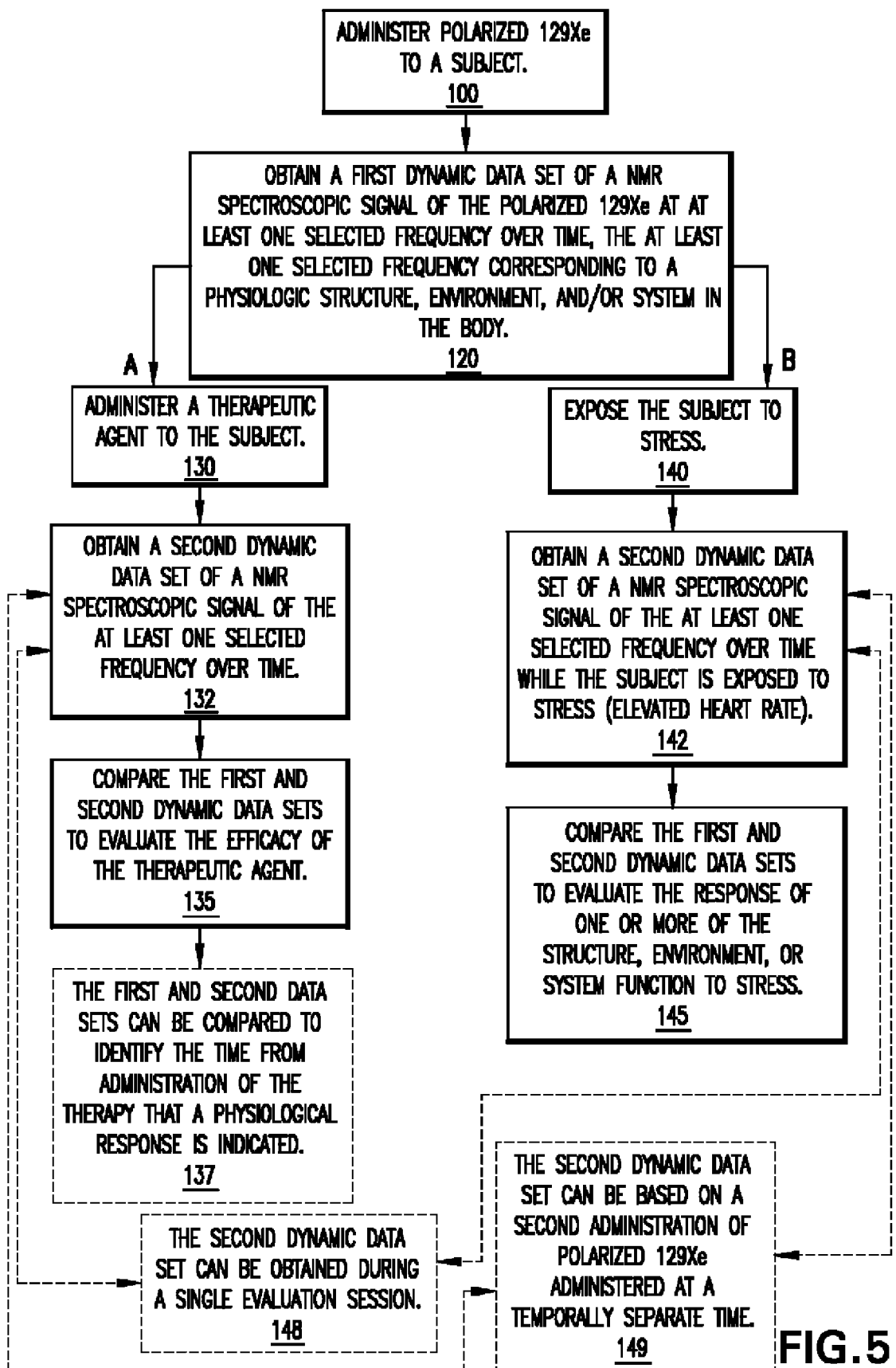

METHODS FOR IN VIVO EVALUATION OF PULMONARY PHYSIOLOGY AND/OR FUNCTION USING NMR SIGNALS OF POLARIZED $^{129}$XE

RELATED APPLICATIONS

This application is a divisional of U.S. application Ser. No. 10/356,240 filed Jan. 31, 2003 now U.S. Pat. No. 7,179,450 which is a continuation in part of U.S. application Ser. No. 10/236,233 filed Sep. 6, 2002, now abandoned, which claims priority to U.S. application No. 60/323,667 filed Sep. 20, 2001 the entire disclosure of which is hereby incorporated by reference.

FIELD OF THE INVENTION

The present invention relates to magnetic resonance imaging ("MRI") and MR spectroscopy using hyperpolarized noble gases. More particularly, the present invention relates to techniques to assess certain conditions in vivo using polarized noble gases.

BACKGROUND OF THE INVENTION

Chronic heart failure (CHR) appears to affect a relatively large and potentially increasing segment of the population. See, e.g., *The Task Force on Heart Failure of the European Society of Cardiology. Guidelines for the Diagnosis of Heart Failure,* 16 Eur. Heart Jnl., p. 741-751 (1995). In addition, many elderly heart failure patients are women, and the more common cause of the syndrome may be diastolic dysfunction. Early diagnosis of heart failure, particularly heart failure due to diastolic dysfunction, in which ejection fraction may be normal, remains a challenge. Documentation of pulmonary congestion in the absence of evidence for systolic dysfunction is believed to represent reasonable criteria for this diagnosis. See Tan et al., *Heart Failure in Elderly Patients: Focus on diastolic Dysfunction, Heart Failure: Scientific Principles and Clinical Practice,* P.A. (Churchill-Livingston, NY, Poole-Wilson, Ed. 1997).

For other cardiopulmonary or respiratory disorders or diseases, patients may exhibit a shortness of breath of uncertain etiology that can make it difficult to identify the disorder or condition and/or to thus treat in an effective manner. For example, in response to administration of pharmacological agents, some patients may experience respiratory distress. Early identification of drug-induced pulmonary reactions or disorders may inhibit lung injury.

Gas transfer from ambient air to the blood involves different in vivo transport mechanisms. Generally described, alveolar ventilation is accomplished by convective and diffusive transport. Gas transfer within the alveolus and from the alveolus into the blood stream occurs by diffusion along concentration gradients. The blood is then transported from the lungs to peripheral tissues by convective transport. These transport processes can be affected by a number of lung diseases. Convective transport in the airways is thus impaired in obstructive lung diseases. See Alderson PO, Line BR. *Scintigraphic evaluation of regional pulmonary ventilation.* Semin Nucl Med 1980; 10:218-242. Diffusion impairment can occur in interstitial lung diseases as well as in pulmonary edema. See Puri et al., *Reduced alveolar-capillary membrane diffusing capacity in chronic heart failure. Its pathophysiological relevance and relationship to exercise performance,* Circulation 1995; 91:2769-2774, V-16. The pulmonary vasculature can be affected by both primary lung disease and by left heart failure, causing abnormalities in blood flow. Worsley et al., *Ventilation-perfusion lung scanning in the evaluation of pulmonary hypertension.* J Nucl Med 1994; 35:793-796.

In view of the above, there remains a need for a minimally invasive in vivo method of evaluating a patient to identify the underlying condition(s) so that appropriate treatments can be pursued, certain medicaments initiated or ceased, and/or to evaluate the efficacy of therapeutic treatments administered to treat those conditions.

SUMMARY OF THE INVENTION

The present invention uses polarized $^{129}$Xe to evaluate whether a subject has chronic heart failure or other respiratory, cardiopulmonary, or systemic impairments or conditions.

Certain embodiments are directed to in vivo methods for evaluating a physiological structure or environment, or physiologic function of a system in a subject using polarized $^{129}$Xe. The method comprises: (a) delivering polarized $^{129}$Xe gas in vivo to a subject; (b) obtaining a first NMR spectroscopic signal of the polarized $^{129}$Xe gas in the subject at at least one chemical shift frequency to generate a first dynamic data set of the NMR spectroscopic signal values over time, with the polarization of the $^{129}$Xe being repetitively destroyed at predetermined delays in a compartment or compartments of interest, the dynamic data set being representative of the polarized gas in a physiologic structure, environment, or system of interest; (c) exposing the subject to stress; (d) obtaining a second NMR spectroscopic signal of the polarized gas in the subject at the at least one chemical shift frequency to generate a second dynamic data set of the NMR spectroscopic signal values over time, with the polarization of the $^{129}$Xe being repetitively destroyed at predetermined delays in the compartment or compartments of interest; and (e) comparing the first and second dynamic data sets to evaluate the response of the structure, environment, or system to stress.

In particular embodiments, the physiologic structure undergoing evaluation is the alveolar-capillary membrane.

Other embodiments are directed at in vivo methods for evaluating a physiologic structure, environment, or function in a subject using polarized $^{129}$Xe, comprising: (a) delivering polarized $^{129}$Xe gas in vivo to a subject; (b) obtaining a first NMR spectroscopic signal of the polarized gas in the subject at at least one chemical shift frequency to generate a first dynamic data set of the NMR spectroscopic signal values over time with the polarization of the $^{129}$Xe being repetitively destroyed at predetermined delays in a compartment or compartments of interest, the dynamic data set being representative of the polarized gas in a physiologic structure, environment, or system of interest; (c) administering a physiological active therapeutic agent to the subject; (d) obtaining a second NMR spectroscopic signal of the polarized gas in the subject at the at least one chemical shift frequency to generate a second dynamic data set of the NMR spectroscopic signal values over time with the polarization of the $^{129}$Xe being repetitively destroyed at predetermined delays in the compartment or compartments of interest; and (e) comparing the first and second dynamic data sets to evaluate the physiological response of the subject to the therapeutic agent.

Particular embodiments are directed to in vivo methods for evaluating cardiopulmonary function or whether a subject has chronic heart failure. The method includes: (a) delivering polarized $^{129}$Xe in vivo to a subject such that the polarized $^{129}$Xe moves across the alveolar-capillary membrane to be taken up in the blood across the membrane, the polarized gas in the blood having a corresponding polarized gas NMR chemical shift signal frequency; (b) destroying the polarization of the polarized $^{129}$Xe in the blood (and/or the membrane); (c) obtaining an NMR spectroscopic signal of the polarized $^{129}$Xe in the subject over time at the blood chemical shift frequency to generate at least one dynamic data set of the NMR spectroscopic signal strength over time; (d) evaluating the dynamic data; and (e) determining whether the subject has chronic heart failure based on the obtaining and evaluating steps. Still other embodiments are directed to in vivo methods for evaluating whether a subject has a respiratory disorder, or a cardiopulmonary disorder such as chronic heart failure. These methods comprise: (a) delivering polarized $^{129}$Xe in vivo to a subject such that the polarized $^{129}$Xe travels across the alveolar-capillary membrane to be taken up in the blood across the membrane, the polarized gas in the blood having a corresponding polarized gas NMR chemical shift signal frequency; (b) destroying the polarization of the polarized $^{129}$Xe in the blood and/or the membrane; (c) obtaining an NMR spectroscopic signal of the polarized gas in the subject over time at the blood and/or tissue resonance frequency to generate at least one dynamic data set at at least one chemical shift frequency of interest of signal strength values over time; and (d) evaluating the dynamic data to assess whether the subject has a respiratory or cardiopulmonary disorder such as chronic heart failure.

Other embodiments are directed to computer programs comprising computer readable program code that obtains and compares first and second dynamic data sets to evaluate one or more of: (a) the presence of chronic heart failure; (b) to evaluate a physiologic response to a therapeutic agent; (c) to monitor the progression of a respiratory or cardiopulmonary disease; and (d) a physiological response to applied stimulus (chemical or physical).

In certain embodiments, the evaluating step may consider the time constant associated with the time it takes the polarized gas to travel across the membrane structure and then enter the blood so that the signal strength increases therein after the destroying step. In addition, the evaluating step may consider one or more of the oxygen saturation level, the ejection fraction, of the tissue volume based on the dynamic data.

In other embodiments, the subject can be evaluated both during exercise and when at rest and/or after administration of a therapeutic agent to evaluate cardiopulmonary or pulmonary function and/or therapeutic efficacy.

Other embodiments of the present invention are directed at methods for monitoring gas exchange dynamics of $^{129}$Xe at or across the blood brain barrier to evaluate inflammatory disorders of the brain such as meningitis, encephalitis, and the like and/or to provide methods that can distinguish between certain disorders such as between meningitis and cerebritis by analyzing the gas exchange at the blood barrier membrane.

In particular embodiments, pulmonary reactions to a pharmacological agent and/or drug-induced pulmonary disorders can be assessed for clinical evaluation of the pulmonary impact on a patient during drug evaluations or trials.

In still other embodiments, concurrent assessment of at least one parameter associated with a patient's physiological structure and at least one parameter associated with a patient's cardiopulmonary function can be carried out using polarized $^{129}$Xe administered in vivo. The assessment can employ a mathematical diffusion model which allows the quantification of multiple lung physiological parameters from the uptake dynamics of NMR build-up signals of hyperpolarized $^{129}$Xe in the body.

In certain embodiments, concurrent assessment of both alveolar-capillary diffusing capacity and pulmonary perfusion can be performed using the NMR spectroscopic signal data set of the $^{129}$Xe in the body. In particular aspects, at least three parameters can be evaluated using NMR data or NMR data with MRI imaging data obtained from a single clinical session so as to concurrently assess: (a) alveolar-capillary diffusing capacity; and (b) pulmonary perfusion. Lung ventilation imaging may be carried out also using the same polarized $^{129}$Xe to generate an MRI ventilation image.

The NMR uptake curves may, in certain embodiments, be used to evaluate lung ventilation because the uptake curves are representative of the convective and diffusive transport of the xenon.

Certain embodiments of the present invention are directed to in vivo methods for evaluating respiratory, pulmonary and/or cardiopulmonary function. The methods can include: (a) delivering polarized $^{129}$Xe in vivo to a subject such that the polarized $^{129}$Xe moves from an alveolar gas compartment through a tissue compartment with thickness $L_T$, a capillary compartment with thickness $L_C$ comprising plasma and red blood cells, and is then taken away in the blood stream; (b) obtaining NMR spectroscopic signals of the polarized $^{129}$Xe in the subject over time at selected chemical shift frequencies to generate at least one dynamic data set of the NMR spectroscopic signal strength over time with the polarization of the $^{129}$Xe being repetitively destroyed at predetermined delays in a compartment or compartments of interest; and (c) calculating a plurality of selected parameters associated with lung function and/or physiology according to a predetermined mathematical diffusion model of alveolar gas exchange using the NMR-derived dynamic data set.

In certain embodiments, the calculations can be carried out so that if there is a deficit, the evaluation can determine whether the deficit is related to membrane diffusion or pulmonary perfusion based on the NMR data set. The NMR spectrum can include at least one signal corresponding to dissolved polarized $^{129}$Xe with an uptake time constant associated with the initial build-up portion of this NMR signal. In certain embodiments, the ratio of uptake time constant and mean transit time can be calculated to determine whether the gas exchange is perfusion or diffusion limited.

Other embodiments of the present invention are directed to computer program products for evaluating (measuring) lung physiology or functionality. The computer program product includes a computer readable storage medium having computer readable program code embodied in the medium, the computer-readable program code includes: (a) computer readable program code that obtains first and second NMR spectroscopic signals of polarized $^{129}$Xe in the subject over time at selected chemical shift frequencies to generate corresponding dynamic data sets of NMR spectroscopic signal strength values over time; (b) computer readable program code that provides a predetermined multiple compartment mathematical diffusion model of aveolar gas exchange; and (c) computer readable program code that uses data from the dynamic data sets and the mathematical model to calculate a plurality of selected parameters associated with lung physiology and function. The evaluated parameters can be used to determine whether there is a detectable deficit and, if so, whether the deficit is associated with alveolar membrane diffusing capacity and/or pulmonary perfusion.

Still other embodiments are directed to systems for evaluating lung physiology or functionality. The systems can include means for evaluating first and second NMR spectroscopic signals of polarized $^{129}$Xe in a subject over time at selected chemical shift frequencies to generate corresponding dynamic data sets of NMR spectroscopic signal strength values over time using a multi-compartment predetermined mathematical diffusion model of aveolar gas exchange; and means for calculating the t values of a plurality of selected parameters associated with lung physiology and function in a manner that determines whether there is a detectable deficit using data from the first and second dynamic data sets and the mathematical model. The selected parameters comprise total diffusion length, tissue thickness, blood thickness, perfusion, mean transit time, relative blood volume, and alveolar radius. The means can include NMR spectroscopic systems with computer modules or independent signal analysis computer systems that have computer modules to analyze the build-up curves of the NMR signals of interest.

The system can also include means for generating the NMR signals of the polarized $^{129}$Xe in vivo, such as a spectroscopy system with a magnet and RF excitation pulse generator with transmitters and receivers as is known to those of skill in the art. In certain embodiments, the system can include a computation module that can determine whether the deficit is associated with alveolar membrane diffusing capacity and/or pulmonary perfusion.

As will be appreciated by those of skill in the art in light of the present disclosure, embodiments of the present invention may include methods, systems and/or computer program products. The foregoing and other objects and aspects of the present invention are explained in detail herein.

BRIEF DESCRIPTION OF THE DRAWINGS

FIG. 5 is a flow chart illustrating operations of a method, system, or computer program for spectroscopic analysis according to embodiments of the present invention.

DETAILED DESCRIPTION OF EMBODIMENTS OF THE INVENTION

Figure 1A:
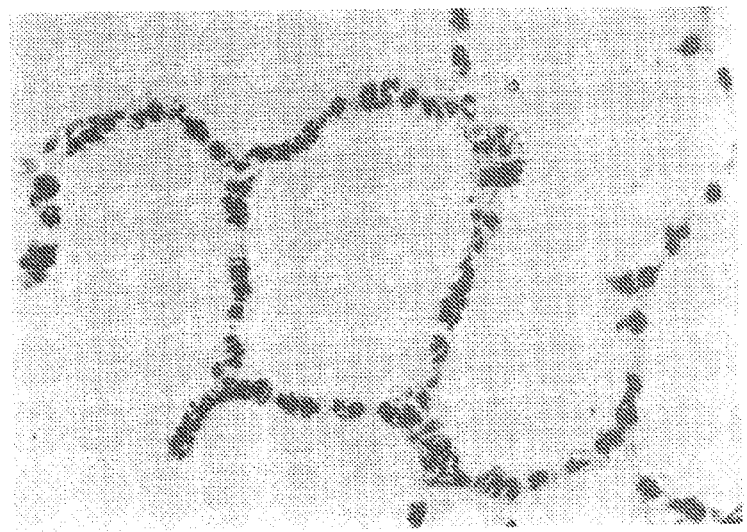
FIG. 1A is a prior art enlarged micrograph of lung tissue and alveolar structure.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, layers, regions or features may be exaggerated for clarity. Broken lines in the figures represent optional features or operations, unless stated otherwise.

As known to those of skill in the art, polarized gases can be collected, frozen, thawed, and used in MRI and NMR spectroscopy applications. In certain embodiments, the freeze collection and thawing may not be required. For ease of description, the term "frozen polarized gas" means that the polarized gas has been frozen into a solid state. The term "liquid polarized gas" means that the polarized gas has been or is being liquefied into a liquid state. Although each term includes the word "gas", this word is used to name and descriptively track the gas that is produced via a hyperpolarizer to obtain a polarized "gas" product. Thus, as used herein, the term "gas" has been used in certain places to descriptively indicate a hyperpolarized noble gas product and may be used with modifiers such as solid, frozen, dissolved, and liquid to describe the state or phase of that product. Also, for certain embodiments, the hyperpolarized gas is processed such that it is a pharmaceutical grade product suitable for in vivo delivery to a human subject. In particular embodiments, the $^{129}$Xe gas product is formulated to have less than about 10 ppb (parts per billion) alkali metal therein, and can have less than about 1 ppb.

The term "compartment" means a physiologic space or region in the body of a subject through which $^{129}$Xe can diffuse or move and an NMR signal has an associated resonance or chemical shift frequency, such as cells, tissue, membrane, air or fluid space, and fluid. For example, the pulmonary system can be described as having a gas compartment, a tissue compartment, and a blood compartment. In certain embodiments, during evaluation, the $^{129}$Xe diffuses from the gas compartment through the tissue compartment and into the blood compartment. Embodiments of the present invention can be used to non-invasively measure physiological structure and/or evaluate functional capacity (operation) of the lung and its constituent components. Various techniques have been employed to accumulate and capture polarized gases. For example, U.S. Pat. No. 5,642,625 to Cates et al., describes a high volume hyperpolarizer for spin-polarized noble gas and U.S. Pat. No. 5,809,801 to Cates et al. describes a cryogenic accumulator for spin-polarized $^{129}$Xe. U.S. Pat. No. 6,079,213 to Driehuys et al., entitled "Methods of Collecting, Thawing, and Extending the Useful Life of Polarized Gases and Associated Apparatus", describes an improved accumulator and collection and thaw methods. The disclosures of these documents are hereby incorporated by reference as if recited in full herein.

As used herein, the terms "hyperpolarize," "polarize," and the like, are used interchangeably and mean to artificially enhance the polarization of certain noble gas nuclei over the natural or equilibrium levels. Such an increase is desirable because it allows stronger imaging signals corresponding to better MRI images and spectroscopy signals of the gas in the body. See Albert et al., U.S. Pat. No. 5,545,396, the contents of which are hereby incorporated by reference as if recited in full herein. As is known, hyperpolarization can be induced by spin-exchange with an optically pumped alkali-metal vapor or alternatively by metastability exchange or other suitable technique known to those of skill in the art.

Particular embodiments of the present invention are directed to methods of evaluating a subject for respiratory disorders and/or cardiopulmonary disorders including chronic heart failure. Generally stated, polarized $^{129}$Xe can be administered to a subject in vivo and monitored to determine one or more of whether low oxygen saturation is may be caused by poor ventilation, poor perfusion, reduced membrane permeability (poor gas diffusing capacity across the alveolar membrane), increased membrane thickness, as well as pulmonary edema and the like. Such an analysis can be used to diagnose chronic heart failure, to differentiate uncertain aetiology of breathlessness or shortness of breath (or other breathing impairments) such as to identify cardiac or respiratory origin, to assess the function of the alveolar-capillary system, and to monitor therapeutic efficacy of treatments on those conditions. The deficiency may be caused by abnormalities in perfusion, diffusion, or ventilation, or by combinations thereof, resulting in poor blood oxygenation.

Other potential clinical indications which can be assessed by methods of the present invention include, but are not limited to, the presence and/or extent of emphysema, the presence and/or extent of alveolitis (and follow-up monitoring for same), to differentiate pure airway conditions from conditions which affect the alveolar airspaces, the diagnosis of alveolar hemorrhagic conditions, and the diagnosis of radiation pneumonitis. In addition, the efficacy of therapeutics administered to treat a condition can be evaluated as a part of the treatment or as a part of pre-clinical drug trials to help establish the clinical efficacy of the proposed drug. In other embodiments, the biophysical or biofunctional reaction to drugs can be assessed during drug discovery programs and/or clinical trials (animal and/or human) and the like.

In particular embodiments, the polarized $^{129}$Xe can be administered over a desired number of inspiratory cycles and the NMR signals of interest and associated data set can be collected in a clinical procedure having a duration of less than about 15 minutes, and, typically, less than about 10 minutes. The patient may hold his/her breath for about 5-20 seconds, and more typically about 7-12 seconds, or other suitable time period to allow the signal to be directed into the pulmonary system.

In certain embodiments, operations of the invention can be carried out using hyperpolarized $^{129}$Xe to evaluate respiratory, pulmonary, and/or cardiopulmonary disorders. For example, NMR spectroscopic signals of $^{129}$Xe in the body can be used to obtain data regarding parameters associated with pulmonary physiology and/or function in order to assess, diagnose, or monitor, one or more of: a potential bioreaction to a transplant, such as transplant rejection (of transplanted organs in the body whether lung, heart, liver, kidney, or other organ of interest), environmental lung disorders, pneumonitis/fibrosis, pulmonary hypertension, pulmonary inflammation such as interstitial and/or alveolar inflammation, interstitial lung diseases or disorders, pulmonary and/or alveolar edema with or without alveolar hemorrhage, pulmonary emboli, drug-induced pulmonary disorders, diffuse lung disorders, chronic obstructive pulmonary disease, pneumoconiosis, tuberculosis, pleural thickening, cystic fibrosis, pneumothorax, non-cardiogenic pulmonary edema, angioneurotic edema, angioedema, type I alveolar epithelial cell necrosis, hyaline membrane formation, diffuse alveolar damage such as proliferation of atypical type II pneumocytes, interstitial fibrosis, interstitial and/or alveolar infiltrates, alveolar septal edema, chronic pneumonitis/fibrosis, bronchospasm, bronchialitis obliterans, alveolar hemorrhage, aspiration pneumonia, hyercapnic respiratory failure, alveolitis/fibrosis syndrome, systemic lupus erythematosus, chronic eosinophilic pneumonia, acute respiratory distress syndrome, and the like.

The lung can be a target of drug toxicity. It is known for example, that many medications, including chemotherapeutic drugs, anti-inflammatory drugs, anti-microbial agents, cardiac drugs and anticonvulsants can cause lung injury including lung toxicity that can be progressive and result in respiratory failure. See *Diffuse Lung Disorders: A Comprehensive Clinical-Radiological Overview*, Ch. 19, *Drug-Induced Pulmonary Disorders*, (Springer-Verlag London Ltd, 1999), the contents of which are hereby incorporated by reference as if recited in full herein. Examples of drug-induced lung disorders that may be able to be evaluated according to embodiments of the present invention include, but are not limited to: pneumonitis/fibrosis, interstitial lung disease, interstitial or pulmonary honeycombing and/or fibrosis, hypersensitivity lung disease, non-cardiogenic pulmonary edema, systemic lupus erythematosus, bronchiolitis obliterans, pulmonary-renal syndrome, bronchospasm, alveolar hypoventilation, cancer chemotherapy-induced lung disease, pulmonary nodules, acute chest pain syndrome, pulmonary infiltrates, pleural effusion and interstitial infiltrates, angioedema, cellular atypia, diffuse reticular or reticulonodular infiltrates, bilateral interstitial infiltrates, reduced diffusing capacity, parenchymal damage with alveolar epithelial hyperplasia and fibrosis and/or atypia, early onset pulmonary fibrosis, late-onset pulmonary fibrosis, subacute interstitial lung disease.

Some of the above-conditions have been known to occur with specific drugs, such as, mitomycin and bleomycin, and, in certain embodiments of the invention, NMR-derived data of hyperpolarized $^{129}$Xe can be used while the patient is being treated with the potentially problematic drug to allow earlier intervention or alternate treatments should the lung exhibit a drug-induced disorder.

In many situations, patients can experience the onset of lung injury at the early onset of treatment with a therapeutic agent or in a certain environment. However, presentation of the injury can be delayed. In certain situations, the symptoms can present acutely with rapid deterioration. In either case, earlier identification of the problem can allow earlier intervention. Indeed, intervention prior to when lung injuries are severe enough to be detected using conventional imaging techniques, such as CT or X-ray, is desired.

Figure 1B:
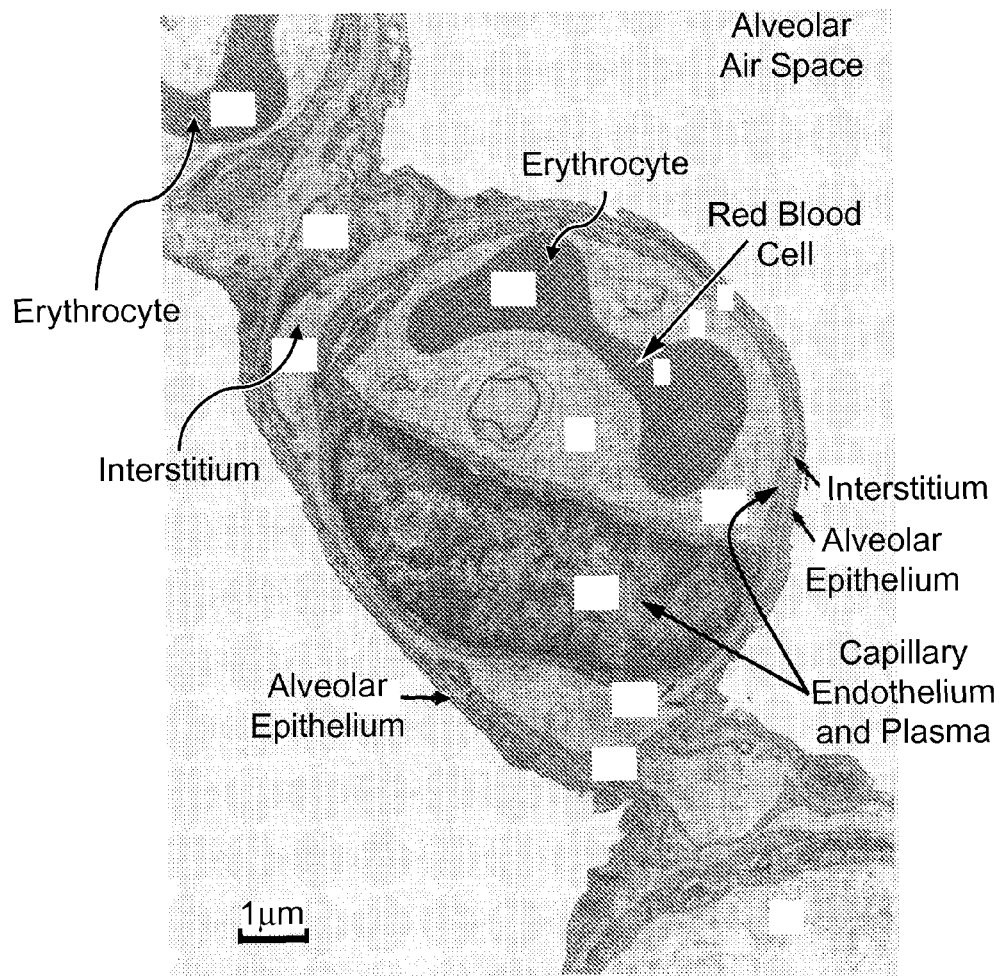
FIG. 1B is a prior art greatly enlarged micrograph of lung tissue and alveolar structure illustrating the alveolar epithelium, the interstitium, the capillary endothelium, a capillary and red blood cells and alveolar air space.

FIG. 1A is a micrograph of lung tissue or alveolar structure. FIG. 1B is enlarged (20×) compared to the scale shown in FIG. 1A and illustrates alveolar structure including the alveolar epithelium ("Ep"), the interstitium ("Ei"), the capillary endothelium ("En"), a capillary ("C") and red blood cell ("R" or "RBC") and alveolar air space ("A"). The present invention provides methods for evaluating gas transit behavior across the alveolar-capillary membrane into the pulmonary blood.

In certain embodiments, this information can be used to evaluate chronic heart failure ("CHF") because CHF typically disturbs the alveolar-capillary membrane and increases the resistance to polarized gas transfer as the gas attempts to travel (i.e., diffuse) toward the pulmonary blood (into the red blood cells). Elevation of the capillary pressure can increase the capillary permeability to water and ions and disrupt local regulatory mechanisms for gas exchange, leading to thickening of the alveolar-capillary interstitium, and/or to a decrease in membrane conductance and subsequent impairment of diffusion capacity.

From the NMR data, information can be obtained about the alveolar-capillary membrane thickness and pulmonary perfusion in resting conditions and during exercise (actual or simulated, the latter meaning chemically induced). NMR data derived from the polarized $^{129}$Xe using the resting and stimulated states may be used to evaluate other pulmonary, respiratory, or cardiopulmonary conditions as noted above.

In operation, in certain particular embodiments, a dynamic data set of NMR spectroscopic signal strength of polarized $^{129}$Xe in the body over time at at least one chemical peak or shift of interest can be obtained and evaluated to assess certain physiological parameters or function. The parameters can include, but are not limited to, one or more of perfusion, thickness of the alveolar-capillary membrane (associated with the average overall diffusion length), alveolar-membrane diffusion time of the polarized gas, the oxygen saturation level or measure of ventilated blood or blood volume (which may be used as a measure of shunt) in the patient. The dynamic data set corresponds to the increase (associated with uptake) in strength of a particular signal or signals with an associated chemical shift (such as in the pulmonary blood, alveolar tissue, or other pulmonary structure or constituent of interest) of the polarized $^{129}$Xe over time.

Figure 2B:
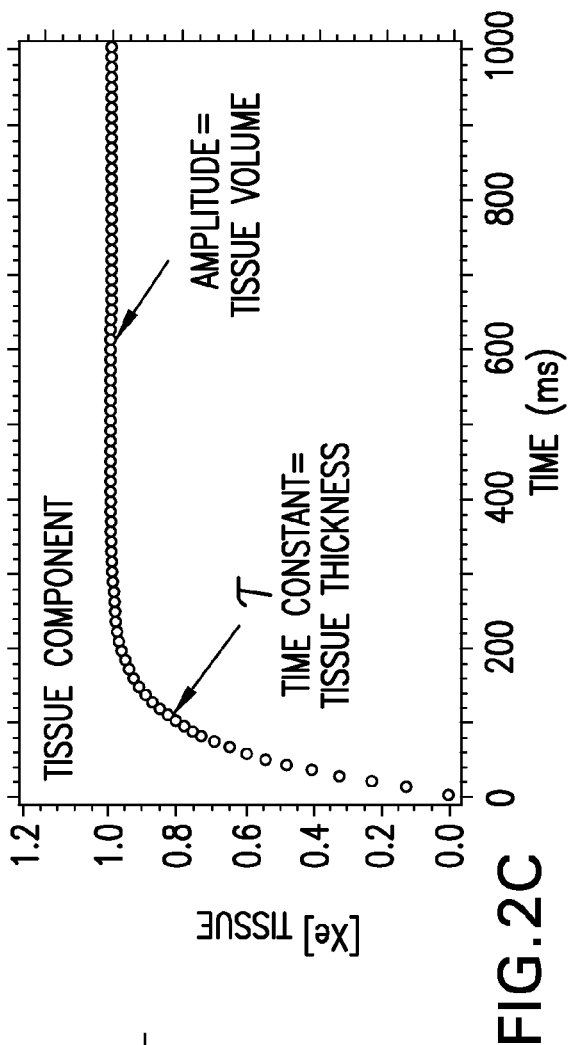
FIG. 2B is a simulated graph of the signal of the $^{129}$Xe blood component over time according to embodiments of the present invention.
Figure 2C:
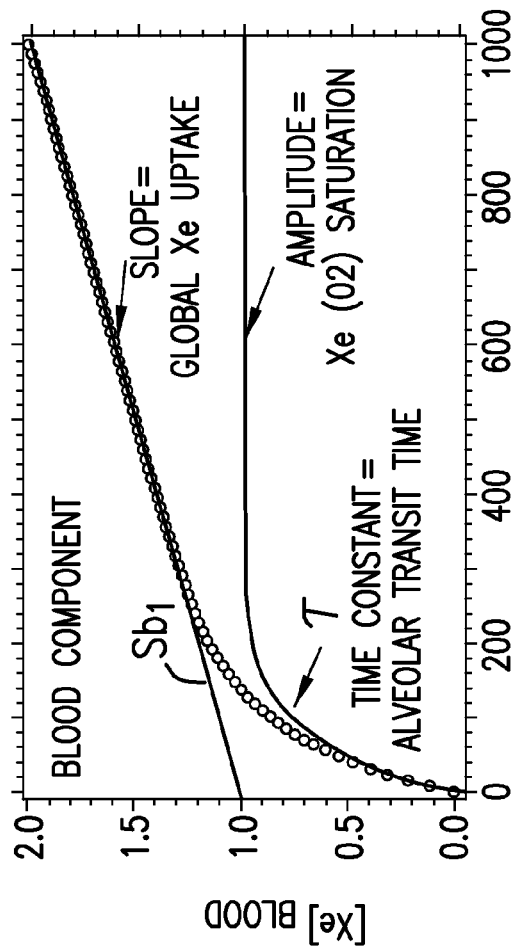
FIG. 2C is a simulated graph of the signal of the $^{129}$Xe tissue component over time according to embodiments of the present invention.
Figure 2A:
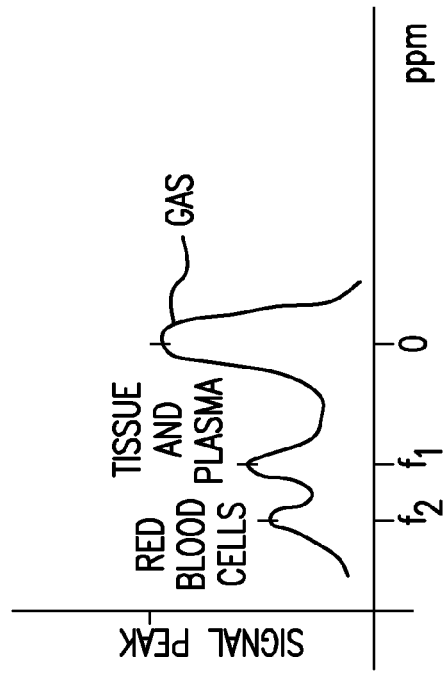
FIG. 2A is a NMR spectrum of polarized $^{129}$Xe peaks of interest according to embodiments of the present invention.

FIG. 2A schematically illustrates a $^{129}$Xe NMR spectrum (simulated) from the chest of a subject. The dissolved-phase spectra are shown on the left side of the figure (indicated by peaks at $f_1$ and $f_2$). When a quantity of polarized $^{129}$Xe is inhaled into the lungs, a small fraction of this gas (roughly estimated at about 0.3% per/second at saturation) transits into the pulmonary blood. It is known that polarized $^{129}$Xe in the lung exhibits three distinct NMR resonances: 0 parts per million ("ppm") is associated with gaseous $^{129}$Xe, 197 ppm is associated with $^{129}$Xe dissolved in lung tissue and plasma ($f_1$), and 212 ppm is associated with $^{129}$Xe dissolved in red blood cells ($f_2$). The signals at each of these resonances can be tracked as a function of time.

Figure 10:
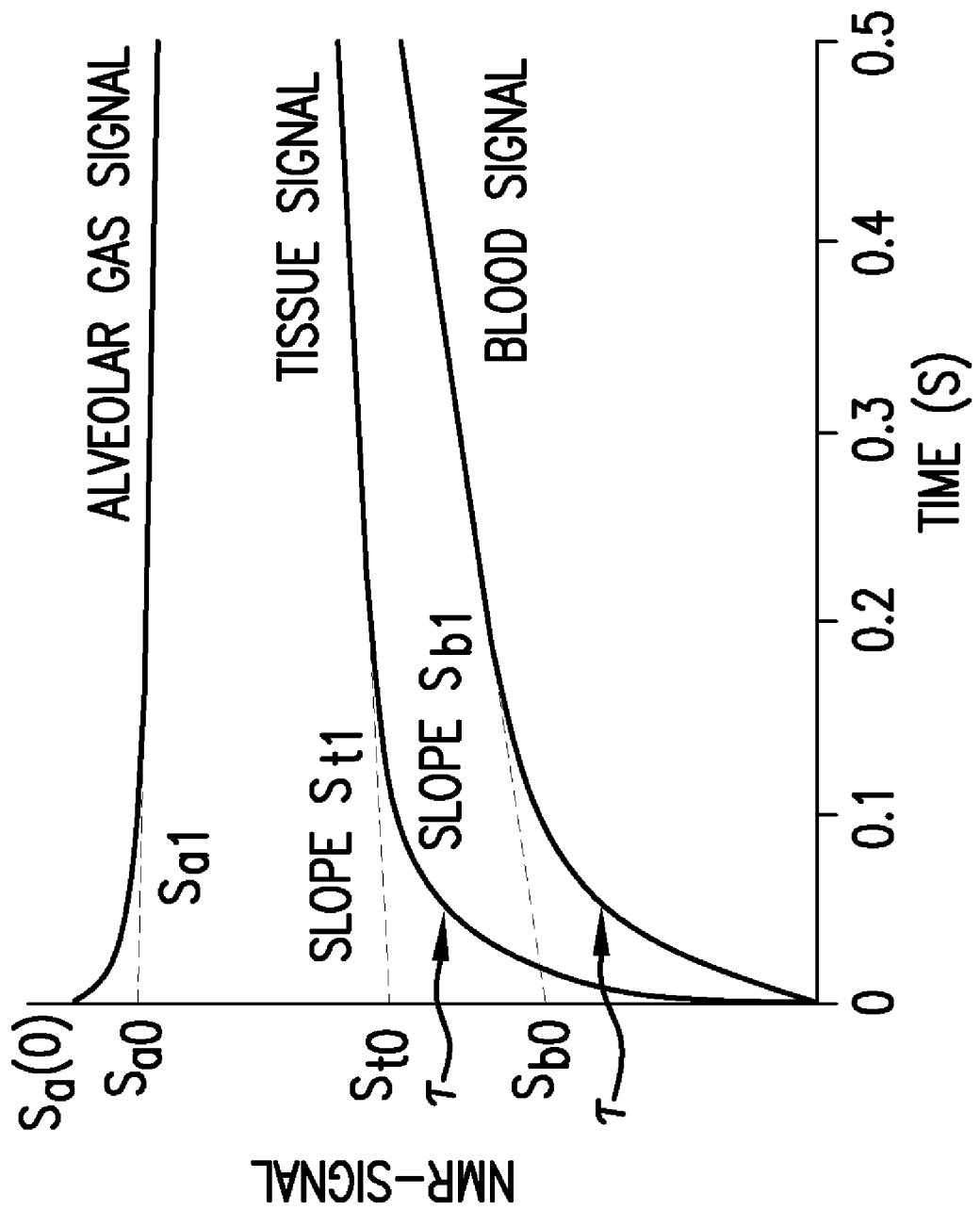
FIG. 10 is a graph of NMR signal strength over time with selected curve parameters in the line shapes of $^{129}$Xe in gas, tissue, and blood, depicted as used to calculate tissue thickness, capillary thickness, perfusion, mean transit time and alveolar radius.

FIG. 2B schematically illustrates a simulated signal strength of the $^{129}$Xe in the blood ($f_2$) over time and FIG. 2C illustrates a simulated signal strength of the $^{129}$Xe in the tissue ($f_1$) over time. FIG. 10 illustrates experimentally obtained uptake curves. To obtain the curve or line shape representing the gas exchange or diffusion process in the body at a selected frequency or shift (or frequencies) of interest, a series of increasingly longer delays between RF pulses are used to generate the response signal. As will be described further below, the NMR pulse sequence is selected so as to repetitively destroy the polarization of the $^{129}$Xe in the compartment(s) of interest before an acquisition of the spectrum at predetermined points of time, with times set to provide increasingly longer (or shorter) delays between the RF pulses. The dynamic data set is obtained by varying the time between the destruction of the dissolved-phase $^{129}$Xe polarization and the corresponding acquisition. If different NMR signals are present in the $^{129}$Xe NMR spectrum representing different dissolved-phase compartments, and if $^{129}$Xe undergoes diffusive exchange between these, then dynamic data sets from each of these compartments can be obtained concurrently, each at corresponding frequencies or chemical shifts.

To generate the dynamic data set of the $^{129}$Xe in the body, polarized $^{129}$Xe is administered to the subject or patient. Then the polarization of the polarized $^{129}$Xe in a selected in vivo environment, structure, or physiology can be destroyed and allowed to rebuild. For example, gaseous polarized $^{129}$Xe is inhaled into the lungs. Part of the polarized $^{129}$Xe can then diffuse serially across Ep, Ei, and En (as defined above and in FIG. 1B) in the membrane and subsequently into the pulmonary blood.

Figure 11:
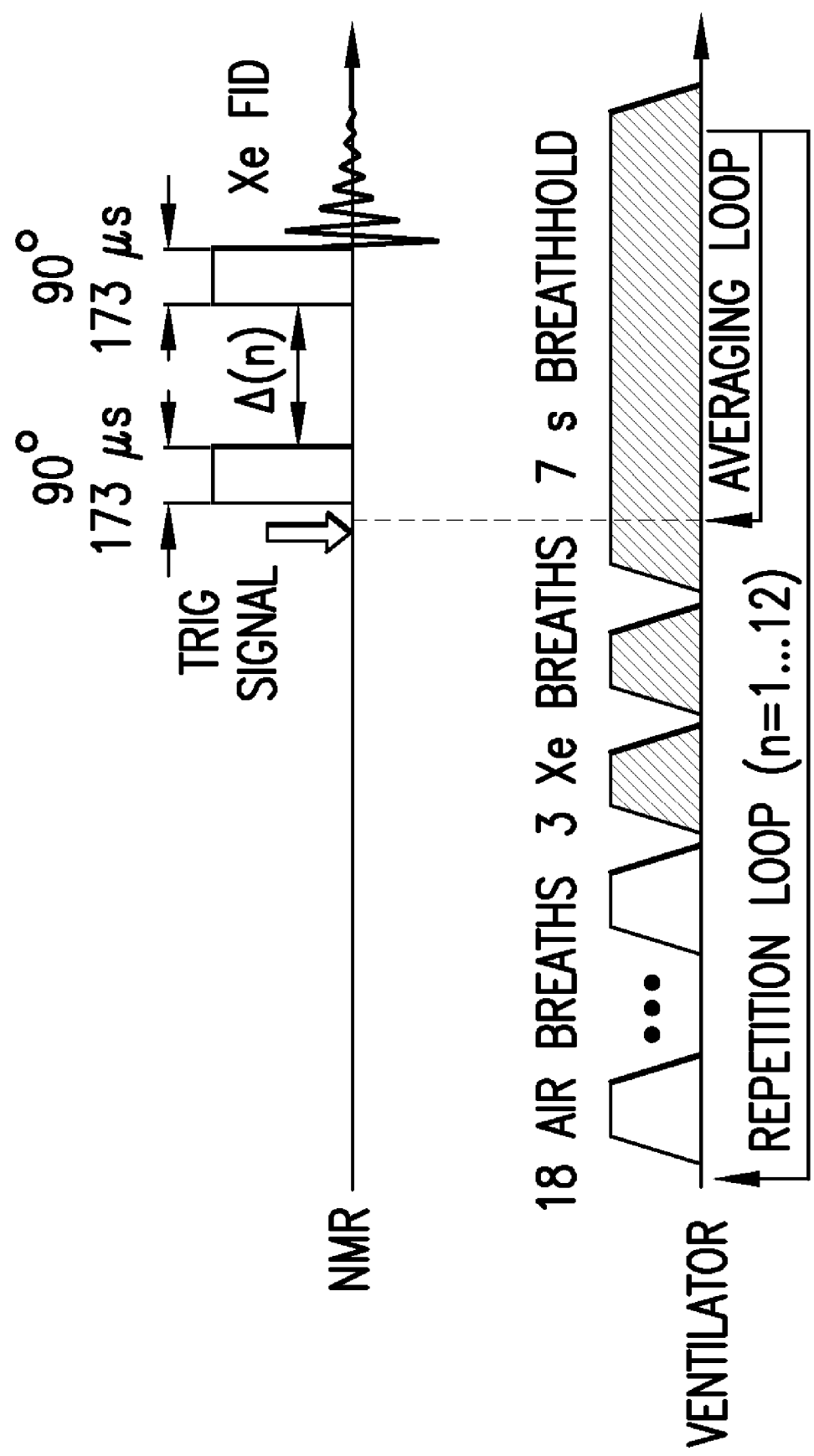
FIG. 11 is a schematic of ventilator operation and the relative timing of NMR data acquisition according to embodiments of the present invention.

As shown in FIGS. 2B and 11, the build up of signal of the polarized $^{129}$Xe in blood can be dynamically monitored to determine a time constant "τ" associated with the diffusion time of the polarized $^{129}$Xe across the alveolar-capillary membrane. In operation, in certain embodiments, the $^{129}$Xe polarization in the alveolar-capillary membrane (including the alveolar epithelium, the interstitium, and the capillary endothelium) and in the capillary blood is destroyed by a large angle excitation pulse, preferably by one or more 90 degree pulses. The time of destruction of the $^{129}$Xe polarization defines t=0, with respect to the subsequent delay. Subsequently, the NMR signal of the polarized $^{129}$Xe is collected after a certain (first) delay time. New polarized $^{129}$Xe from the lungs will enter the tissue and blood during this delay, and hence the corresponding $^{129}$Xe NMR signals from these compartments will have partially rebuilt after the delay (the new polarized gas is provided from the supply of polarized gas held in and delivered from the lungs during the delay period).

Figure 12:
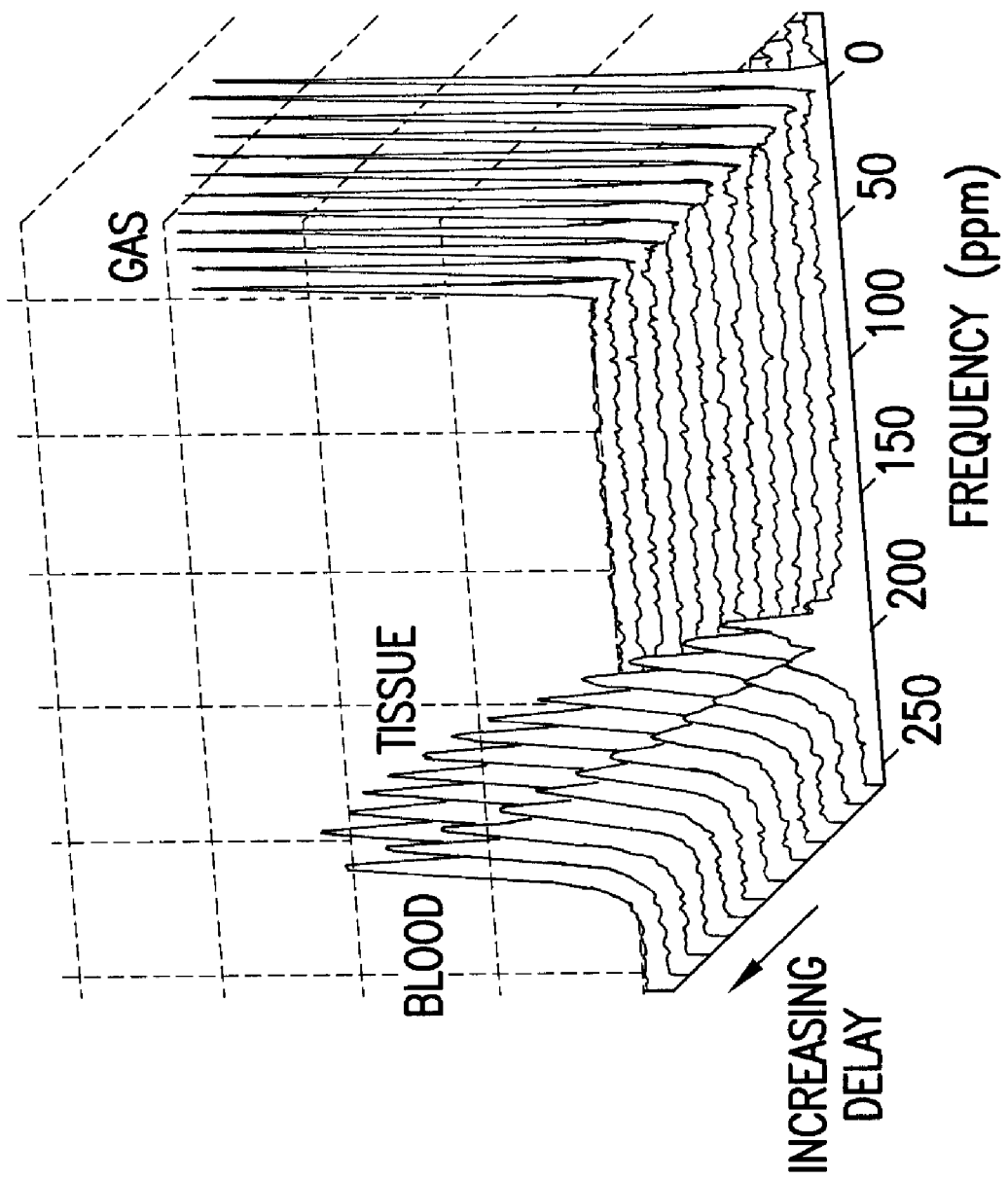
FIG. 12 is a graph of increasing delay versus frequency shift (ppm) a representative set of spectra obtained from a rat according to embodiments of the present invention.

Then the $^{129}$Xe polarization in tissue and blood is destroyed again, and the uptake of new (fresh) polarized $^{129}$Xe is measured after a different (second) delay. Thus, in order to measure the $^{129}$Xe uptake curve(s) in tissue and/or blood, the procedure described above is repeated multiple times using different delays between selective destruction of the $^{129}$Xe polarization and NMR measurement or signal acquisition. FIG. 12 illustrates spectrums obtained over various delays for different compartments.

The NMR data can be collected using increasing/decreasing delays (starting with the shortest and ending with the longest, or starting with the longest and ending with the shortest), or by using other orders as desired. After data collection, the $^{129}$Xe uptake curve(s) can be analyzed using curve fitting analysis techniques well known to those of skill in the art. A corresponding analysis can be also performed on the data from the tissue/plasma compartment (FIGS. 2C and 10).

Figure 13A:
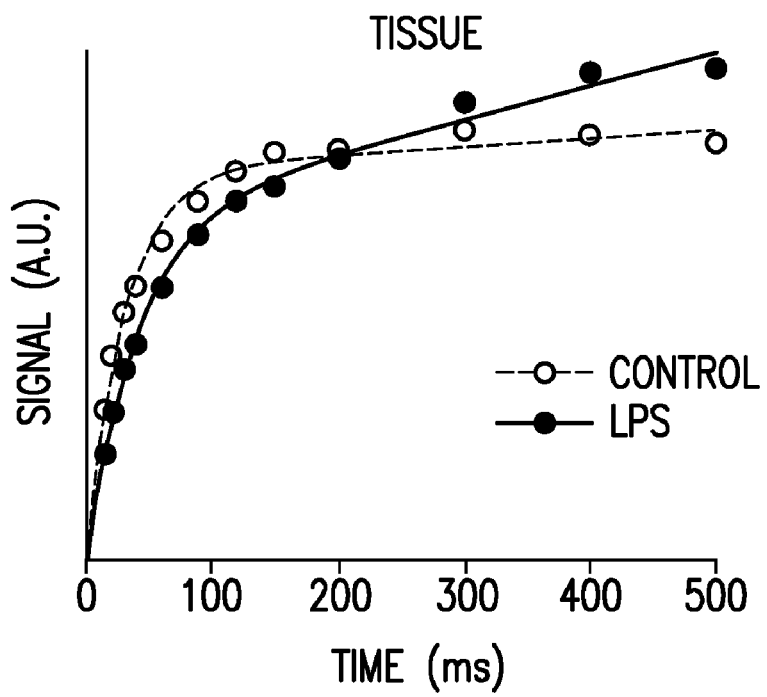
FIGS. 13A and 13B are graphs of signal versus time of xenon signals in tissue and blood, respectively, according to embodiments of the present invention.
Figure 13B:
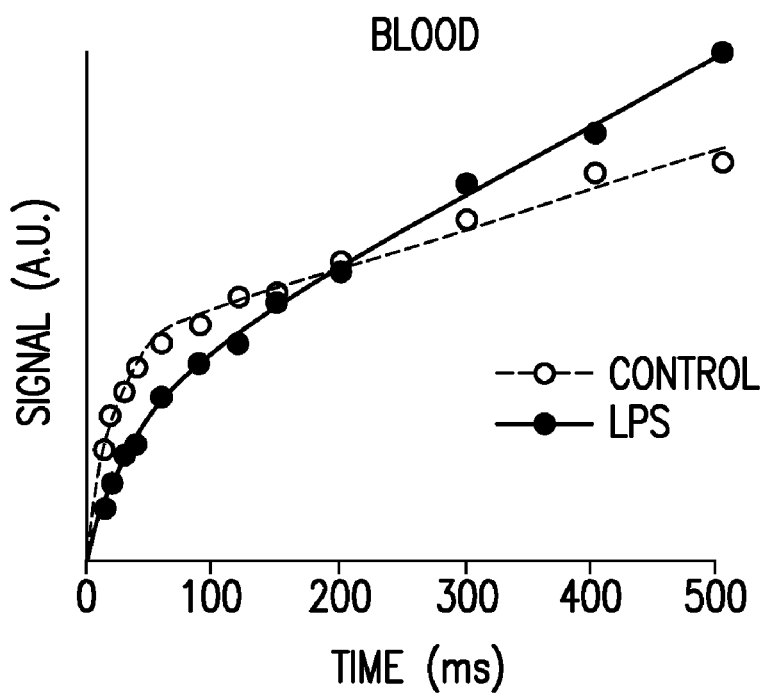

Experimental data corresponding to the simulations in FIGS. 2B and 2C are shown in FIGS. 12, 13A, and 13B. The experiments illustrate that data can be acquired with sufficient temporal resolution to determine an uptake time constant of $^{129}$Xe in tissue and blood. To obtain sufficient data points to generate the time constant "τ", the signal data should be collected for periods of time that are at least two times as long as that of the time constant. Thus, for time constants of 60 ms, data should be collected for at least about 120 ms. In certain embodiments, the uptake time constant "τ" and/or other features of the uptake curves, such as—slopes and intercepts of the curves after initial $^{129}$Xe build-up (see, e.g., FIGS. 2B, 2C, 10) can be used to determine certain parameters associated with the physiologic structure or function, such as, but not limited to, the average overall diffusion length (associated with the thickness of the alveolar-capillary membrane), pulmonary perfusion, capillary diffusion length, mean transit time, and the like. In particular embodiments, the dynamic data can be used to concurrently evaluate and distinguish two aspects of lung function; namely, both diffusing capacity and pulmonary perfusion, as will be discussed further below.

Other embodiments of the invention assess or evaluate other conditions of other membranes or walls associated with lumens or natural body cavities that may be impaired in integrity or function. For example, the glomerular capillary membrane can be evaluated by administering polarized $^{129}$Xe to assess the permeability and flow rate across this membrane to give a quantitative assessment in health and disease. One result may be to record glomerular filtration rate and this could be given globally or for each individual kidney. This is useful in many clinical situations, e.g., measuring GFR prior to chemotherapy administration. In disorders such as glomerulonephritides, the disease affects the structure and function of the membrane so the methods of the present invention can be used to monitor disease progression and effect of therapy. The disorders involved here may be acute and chronic renal failure, nephrotic syndrome, glomerulonephritis and other renal diseases. Similarly, the proximal or distal renal tubules may be evaluated using polarized $^{129}$Xe.

In still other embodiments, the function of the large and/or small bowel wall can be evaluated. A quantitative assessment of bowel membrane integrity and function may be useful in a variety of gastroenterological diseases. In other embodiments, the placental membrane may be evaluated. The polarized $^{129}$Xe may be administered to the mother via inhalation or injection proximate to the placental membrane itself. A minimally invasive method of assessing placental integrity and function using $^{129}$Xe can provide additional information over conventional techniques (such as to observe the consequences of poor function by measuring fetal growth). Such a method of giving quantitative placental function may be a useful clinical tool in obstetrics.

In alternative embodiments, the blood brain barrier can be evaluated so as to quantify or evaluate the integrity and function of this barrier or conditions associated therewith. The evaluation of the blood brain barrier can be to evaluate inflammatory disorders of the brain such as meningitis, encephalitis, and the like and/or to provide methods that can distinguish between certain disorders such as between meningitis and cerebritis by analyzing the gas exchange at the blood barrier membrane. Other embodiments include assessing blood cell physiology or function defects or abnormalities (such as evaluating the presence or degree of sickle cell anemia).

As shown in FIG. 2B (via simulation), and FIGS. 12, 13A and 13B, in certain embodiments, after inhalation of hyperpolarized $^{129}$Xe, its uptake into the pulmonary blood can be measured as a function of time. The initial build-up rate of the $^{129}$Xe NMR signals arising from the tissue and from the blood compartments is sensitive to the thickness of the alveolar-capillary membrane. Data from the $^{129}$Xe uptake dynamics in tissue and blood can be used (directly and/or indirectly) to quantify or assess changes in the structure of the compartments, such as the average thickness of the alveolar-capillary membrane (associated with the average total diffusion length) associated with various cardiopulmonary conditions such as chronic heart failure. Pulmonary "function" means the ability of the lung to perform its intended activity, such as the ability to provide oxygen to the blood stream to ventilate and/or oxygenate blood. The function, including a departure from substantially normal functional capacity, may also be assessed using the $^{129}$Xe NMR uptake data. The polarized $^{129}$Xe uptake data can also be used to evaluate other conditions such as pulmonary fibrosis or other respiratory conditions as noted above.

In other embodiments, the uptake dynamics of $^{129}$Xe during other (later) intervals of the build up curves may be used to evaluate total cardiac output and/or ventilation/perfusion ratios. For example, the curve shown in FIGS. 2B, 2C and 10 can be broken down into an exponential build-up portion during about the first 100 ms, and a dynamic equilibrium portion thereafter. As shown in FIG. 10, the slope of the later portion of the uptake curves (the so-called asymptotic slope) can be identified as "$St_1$" (tissue compartment plus plasma), "$Sb_1$" red blood cell compartment), and "$Sa_1$" (alveolar gas compartment). The corresponding intercepts, "$St_0$", "$Sb_0$", and "$Sa_0$", respectively, are used as measures of the signal amplitudes. The time constant "$\tau$" is associated with the initial (exponential or bent) portion of the uptake curves.

Thus, as illustrated for three different signals in FIG. 10 after the initial build-up, the slope corresponds to the linear signal. For example, the slope of the blood compartment uptake curve is characterized by a linearly increasing portion (inclined) at dynamic equilibrium or dynamic saturation slope at times "t" much greater than $\tau$, while the slope of the tissue compartment approaches a steady state or constant value at times "t" much greater than $\tau$.

The slope can be used as a measure of global xenon uptake (such as a tracer for oxygen) in the blood. The slope of one or more uptake curves may yield information about global blood flow to the ventilated portion of the lung and, hence, may be a predictor of shunt or cardiac output. The time constant "$\tau$" yields information about the thickness of the alveolar-capillary membrane, and hence about whether diffusive gas exchange is impaired. In any event, the uptake curve parameters of the alveolar gas compartment, the tissue compartment, and the blood compartment, such as the respective time constants, slopes, and intercepts of the asymptote lines for the slopes can be used to evaluate or determine lung physiology, such as membrane thickness, tissue distance and/or volume, and/or function (i.e., greater time constants may reflect thicker and/or perfusion resistant compartments or boundaries). The NMR signals and associated evaluations and measurements can be obtained while the subject is substantially at rest and/or when the subject or patient is exposed to stress such as while exercising (or exposed to artificial stimulus elevating the heart beat rate and/or emulating other cardiopulmonary conditions).

In addition, in certain embodiments, the $^{129}$Xe uptake measurement(s) can be used to monitor an administered therapy for efficacy or for drug development or discovery processes where a new drug or use is undergoing evaluation during laboratory, clinical or pre-clinical trials.

The concentration ("C") of xenon in tissue and blood as a function of time (C(t)) can, to a first approximation be written as:

$$C(t) = C_0(1 - e^{-t/\tau}). \qquad \text{Equation (1)}$$

Where "$\tau$" is the $^{129}$Xe uptake time constant and "C" is the concentration of the polarized $^{129}$Xe at the selected frequency. These time constants have been measured in dogs to be at about 61 ms and 70 ms for the tissue and blood compartments, respectively. See Ruppert et al., *NMR of Hyperpolarized $^{129}$Xe in the Canine Chest: Spectral Dynamics Dur-* ing a Breath-Hold, 13 NMR in Biomedicine, p. 633-641 (2000). The time constants are representative of the amount of time it takes xenon to diffuse across the alveolar membrane and into the red blood cells. The diffusion constant of xenon in water is about $2\times10^{-5}$ cm$^2$/s. See Wolber et al., *Measuring Diffusion of Xenon in solution with hyperpolarized* 129Xe *NMR*, 296 Chemical Physics Letters, p. 391-396, (Nov. 6, 1998). The mean square distance traveled by a randomly diffusing gas can be approximated as described by Equation (2).

$$Z^2 = 2Dt.$$ Equation (2)

Where "$Z^2$" is the mean square distance, "D" is the diffusion coefficient constant and "t" is the time it takes the gas to diffuse through the membrane. Thus, from the two exemplary diffusion times measured above, mean thickness or diffusion distances of about 15.6 µm and about 16.7 µm can be calculated. It is noted that these curves are taken from the entire lung and include regions where tissue is thicker or thinner. Alternative pulse sequences can be used to identify the uptake in the first few milliseconds (the times are typically under about 100 ms) corresponding to diffusion times across the thinner membranes. At the onset of (and during) certain diseases, the mean alveolar diffusion time can become longer. Because diffusion time can be approximated as being proportional to the square of the tissue thickness, the diffusion time will be sensitive for quantifying wall thickness and/or thickening (or thinning as the case may be). As will be discussed further below, in certain embodiments, a multi-compartment mathematical model is used to calculate the membrane thickness using the total diffusion length (of the combined tissue and capillary or blood compartments) obtained from the NMR $^{129}$Xe more uptake curves.

Figure 3:
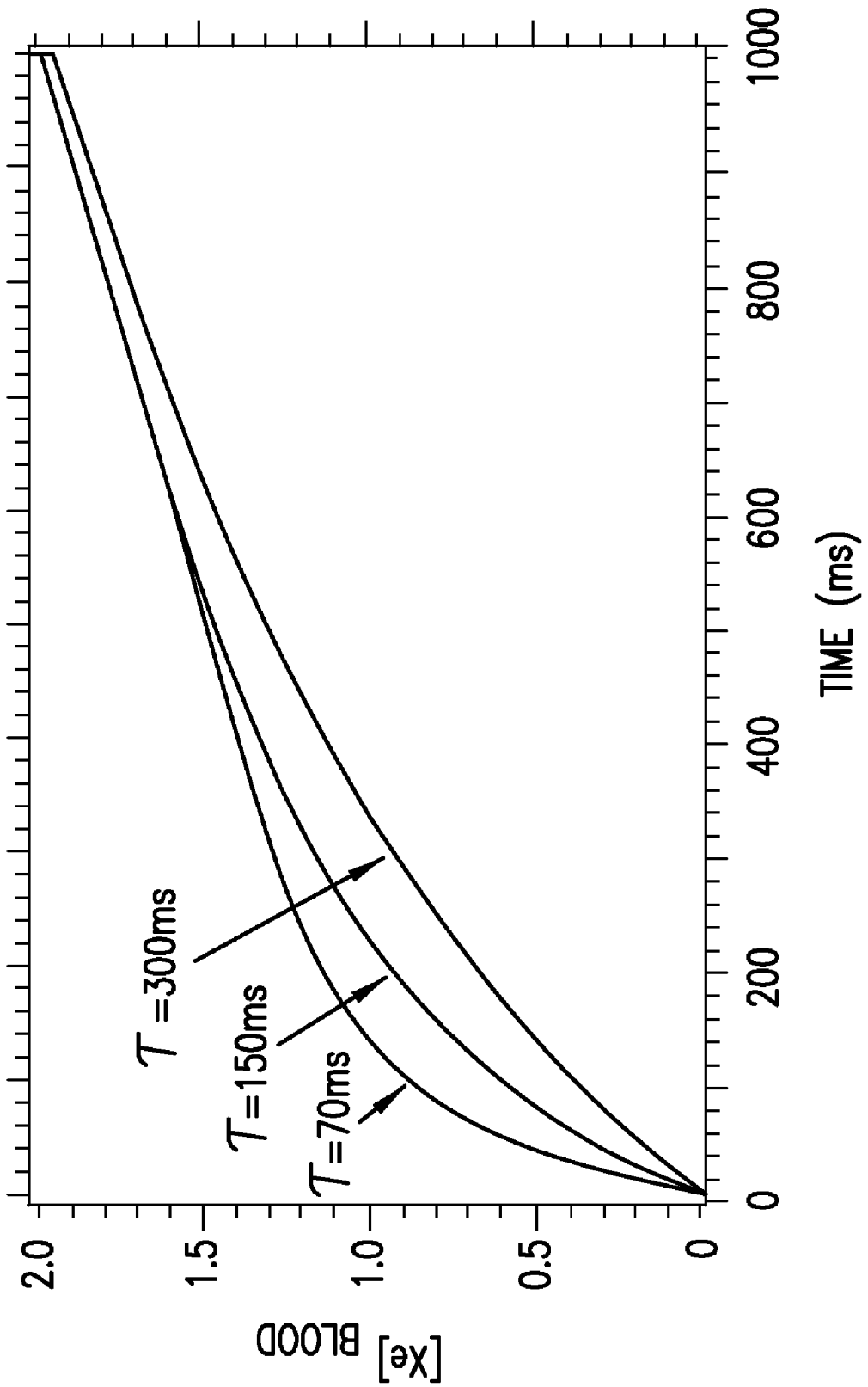
FIG. 3 is a simulated graph of the uptake of polarized $^{129}$Xe in blood over time. The graph illustrates three different curves, each representing a different uptake curve of $^{129}$Xe that can be evaluated to ascertain information about the patient according to embodiments of the present invention.

FIG. 3 illustrates graphs of signal build up curves having three different time constants for the polarized $^{129}$Xe signal in blood illustrating the cardiopulmonary functional change that may be representative of heart failure or other disorders, diseases, or conditions. The time constant may be e determined experimentally using the NMR uptake curves. As shown, the time constant for each of the curves varies in a quantifiable manner. The longer time constants (i.e., τ=150 and 300 ms) correspond to thicker alveolar-capillary membranes. In certain diseases or conditions, the alveolar membrane can thicken in response to hypertension or other conditions. As the condition deteriorates, the diffusion time or time constant "τ" increases (shown as going from 70 ms to 300 ms) corresponding to the thickening of the alveolar membranes in response to hypertension and the like (reducing oxygen diffusing capability). Many therapeutic regimens attempt to thin the alveolar membranes and the present invention can assess whether this objective has been achieved by evaluating the time constant τ and/or other $^{129}$Xe signal parameter. Therefore, monitoring of the $^{129}$Xe uptake dynamics during therapy may provide important clinical information.

The dissolved phase (NMR signal versus RF pulse delay time) $^{129}$Xe uptake curve will have an associated slope that is primarily dependent on blood flow. In operation, in certain embodiments, a 90-degree pulse can be transmitted to the blood; this destroys all the $^{129}$Xe magnetization and, thus, the signal of the dissolved polarized xenon in the blood. Subsequently, after the 90-degree pulse, additional polarized $^{129}$Xe is taken-up (replenished) in the blood (and tissue) over time until a dynamic equilibrium is reached. That is, when dynamic equilibrium is established, the uptake curve can have a constant signal amplitude (see, e.g., FIG. 10, gas signal), or polarized $^{129}$Xe is taken up in the blood at a time-independent rate, resulting in a linear increase of signal versus time (see, e.g., FIG. 10, blood signal). The more polarized xenon in the tissue or blood, the larger or stronger the associated signal. The behavior of the uptake curve at dynamic equilibrium (after the initial transit time across the barrier) can be mathematically represented by the slope of the line or the slope of the asymptote of the uptake line. For the blood signal uptake curve, the slope (after an initial build-up period associated with the initial time for diffusion across the barrier) can be directly proportional to blood flow rate (F) in the bloodstream.

In order to determine the time constant τ associated with the signal build-up of the dissolved phase xenon, several data points (e.g., typically between about 3-10) can be acquired during the first 60 ms. The time constant τ is thereafter determined by curve fitting the data points. In certain conditions, it will take longer for the blood to take-up polarized xenon, such as where there is low blood flow in ventilated regions in the lung and a shallower slope of the signal from $^{129}$Xe in blood versus time may be observed.

In certain particular embodiments, the slope of the dissolved phase polarized $^{129}$Xe NMR signal in tissue and/or blood versus time can be adjusted by comparing it to the gas phase signal in the lung. This gas phase signal is acquired using an RF excitation pulse of a known flip angle $\forall_L$. Thus, in particular embodiments, the present invention can use a mathematical relationship between the dissolved phase polarized xenon signal in the blood or tissue and the xenon signal in the gaseous phase in the lung to establish a quantitative (relative) measure of signal.

In particular embodiments, the lung volume ($V_L$) is measured by methods known to those of skill in the art before or after the MR procedures. Alternatively, an average or normalized lung volume for a particular patient size or age can be assumed. The scaling of the NMR signals or uptake curve can be adjusted based on the lung volume of the patient as larger lung volumes may dilute the concentration of perfused xenon and, hence, the signal strength of the uptake curve(s).

In summary, according to certain embodiments of the present invention, there are several quantifiable parameters that can be derived from the $^{129}$Xe uptake spectra: τ (tissue), τ (blood), and the slopes of the linear uptake portion of the xenon/blood and xenon/tissue resonances. These uptake spectra may be obtained on a regional basis in the lung. This dynamic signal data can be obtained with millisecond or better resolution. In certain embodiments, the alveolar transit time, ventilation or oxygen saturation level, global perfusion, tissue volume and ejection fraction may be evaluated to identify any abnormalities or alterations in physiology or function.

Generally stated, the ventilated blood flows to the heart to the left atrium to the left ventricle and pumped to body through the (arch of) aorta. The blood is forced or ejected from the heart in pulsatile flow corresponding to the pumping action thereof. The pulsatile flow behavior of the blood ejected from the aorta can be monitored to evaluate or map the ejection fraction. Gradient-tagged RF excitation pulses can be used to look at the signal of the $^{129}$Xe in the blood as it exits the aorta or left ventricle (or region proximate thereto). This targeted region can be monitored to obtain the signal strength of the $^{129}$Xe in this ejected blood over time, the signal will increase and decrease corresponding to the cardiac cycle and the signal can be evaluated to assess how much of the polarized blood is pumped out of the left ventricle or aorta in each pumping cycle. This ejection fraction can be compared to the subject's own previous evaluation or based on a statistical population average (by gender and/or age which can be generally stated to be an average of about 60%) to asses whether there is an abnormality. Ejection fraction can be described as the ejected volume divided by the end-diastolic volume of the ventricle. Thus, in certain embodiments, the dynamic gas exchange data of signal over time in one, two, or more different environments, regions, or tissues (such as tissue and blood) can provide information on ventilation, perfusion, and ejection fraction, as noted above.

Figure 4A:
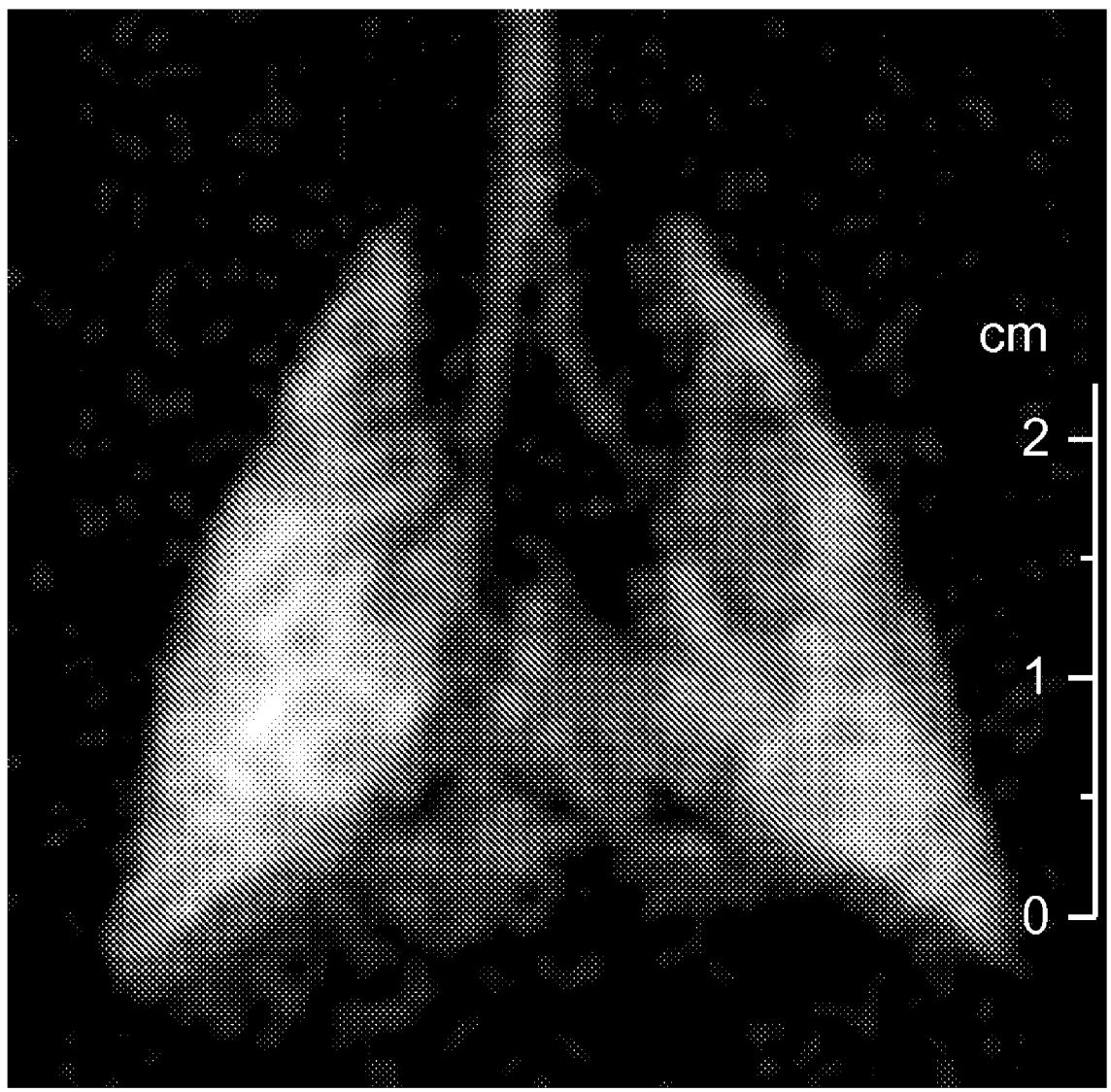
FIG. 4A is a polarized gas $^{129}$Xe ventilation image of the lungs and FIG. 4B is a graph of the polarized $^{129}$Xe uptake in blood over time; each can be generated based on a single-breath or ventilation administration of the polarized $^{129}$Xe according to embodiments of the present invention.
Figure 4B:
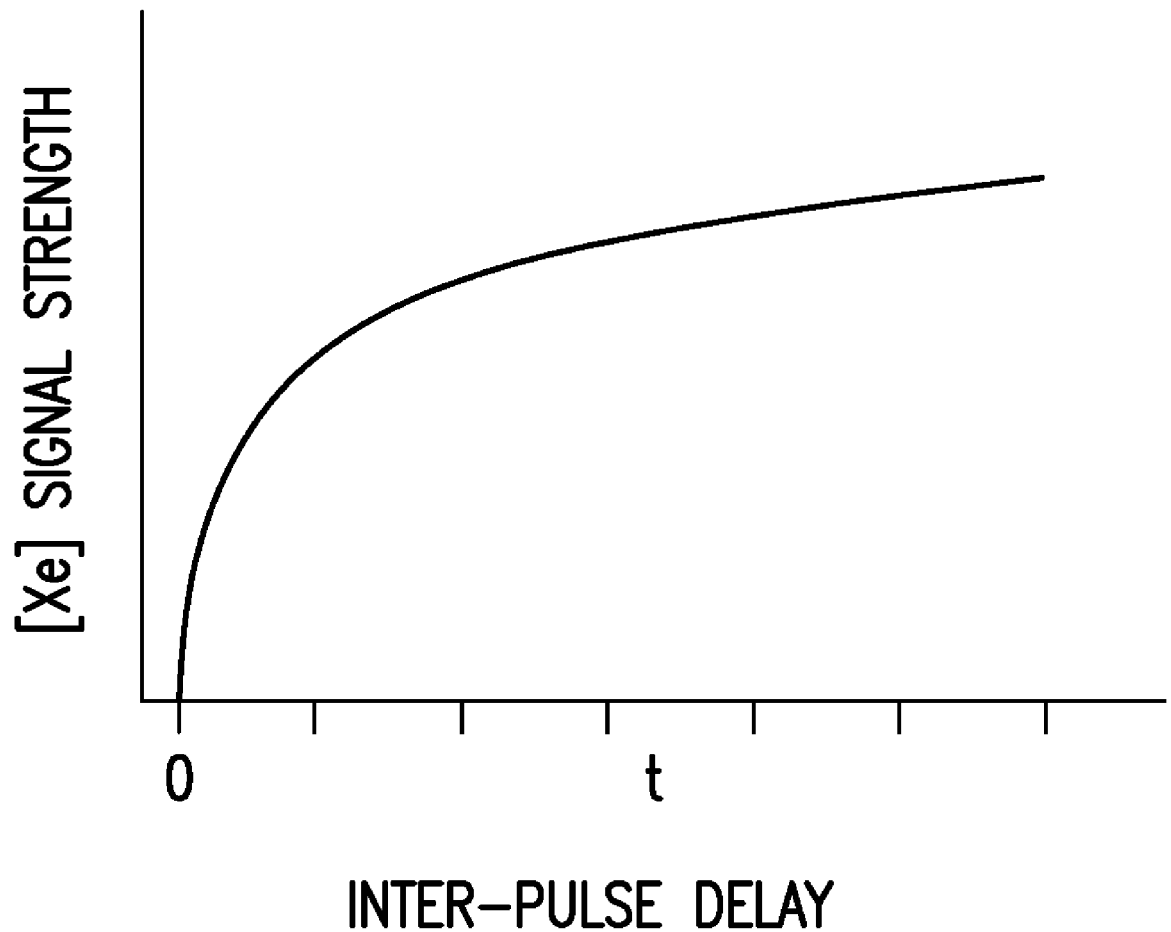

In addition, as shown in FIG. 4A, in certain embodiments, there may be enough magnetization or polarization associated with the $^{129}$Xe in vivo to perform a polarized $^{129}$Xe ventilation or a regular proton MRI image in the same breath-hold period, typically of about 10 seconds. The combination image/scan with the spectroscopic analysis can provide additional information on the state of the cardiopulmonary system. In certain embodiments, the test can be carried out in an MRI magnet with a dual-tuned $^{129}$Xe/$^{1}$H coil to allow conventional imaging to be performed to yield anatomical information in the same MR imaging/spectroscopy session.

FIG. 5 is a block diagram of exemplary operations according to one embodiment of the present invention. Polarized $^{129}$Xe is administered to a patient or subject (Block 100). A first dynamic data set of an NMR spectroscopic signal of the polarized $^{129}$Xe at a (at least one) selected chemical shift frequency can be obtained over time (Block 120). The selected chemical shift frequency corresponds to a targeted physiologic structure, environment, and/or system in the body. The operations can then be carried out to follow only the sequence listed on the left side (col. A) of the figure (Blocks 130-137) or to follow only the sequence listed on the right side (col. B) of the figure (Blocks 140-145). In alternative embodiments, the operations can be combined to evaluate both a therapeutic agent and the subject's response during stress.

Referring first to the left side of the FIG. 5, a therapeutic agent is administered to a subject (which can, but is not required to be, performed after the first dynamic data set is obtained) (Block 130). A second dynamic data set of an NMR spectroscopic signal of the at least one selected frequency is obtained (Block 132). The first and second data sets can be compared to evaluate the efficacy of the therapeutic agent (Block 135). In certain embodiments, the first and second data sets can be compared to identify the time at which a physiological response is indicated after administration of the therapeutic agent (Block 137).

Turning now to the right side of the figure (col. B), the subject is exposed to actual or simulated stress (chemical or physical induced stress) so as to elevate the heart rate and cause other desired physiological changes such as increased respiration rate and the like (Block 140). A second dynamic data set of an NMR spectroscopic signal of the at least one selected frequency is obtained while the subject is exposed to stress (Block 142). The first and second data sets are compared to evaluate the physiological response of one or more of the environment, structure, system or function to stress (Block 145).

In certain embodiments, the second data set can be obtained during a single evaluation session (Block 148). In other embodiments, the second data set can be based on a second administration of polarized $^{129}$Xe at a temporally separate remote time from the first (Block 149).

Figure 6:
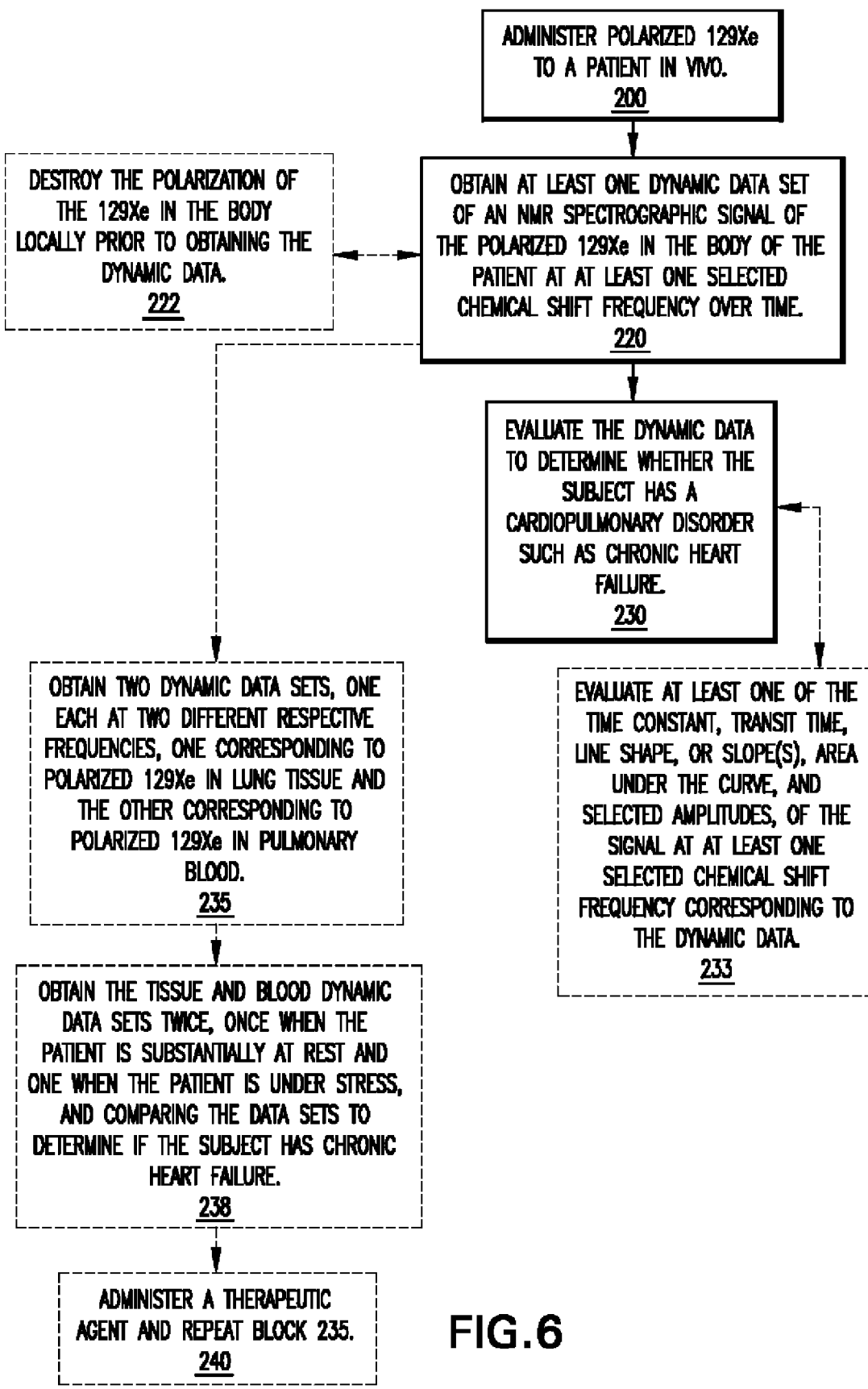
FIG. 6 is a flow chart illustrating operations of a method, system, or computer program for spectroscopic analysis according to embodiments of the present invention.

FIG. 6 is a block diagram of a method for assessing whether a subject has CHF. As shown, polarized $^{129}$Xe is administered to the subject (Block 200). At least one dynamic data set is obtained of an NMR spectrographic signal of the polarized $^{129}$Xe in the body at at least one selected chemical shift frequency over time (Block 220). The polarization level of the $^{129}$Xe in the body can be destroyed locally prior to obtaining the dynamic data (Block 222). The dynamic data set can be evaluated to assess the polarized gas behavior proximate the alveolar-capillary membrane in vivo to determine whether the patient has CHF (Block 230). In certain embodiments, at least one parameter of interest is evaluated based on a curve fit to the dynamic data set: the parameters can include the time constant of the signal, the transit time of the polarized $^{129}$Xe, the line or curve shape of the signal, the area under the curve, and the amplitude (at the time constant or peak) (Block 233).

In particular embodiments, two dynamic data sets, one each at two different respective frequencies can be obtained, one corresponding to polarized $^{129}$Xe in lung tissue, the other corresponding to polarized $^{129}$Xe in pulmonary blood (Block 235). In addition, the two data sets can be obtained twice, once when the patient is substantially at rest and one when the patient is under stress and comparing the data sets to determine if the subject has chronic heart failure (Block 238). Further, a therapeutic agent can be administered and the operation in Blocks 235 and/or 238 can be repeated (Block 240).

Generally stated, in operation, a patient is positioned in an NMR spectroscopy or MRI unit and exposed to a magnetic field. The unit typically includes a super-conducting magnet, gradient coils (with associated power supplies), a NMR coil (transmit/receive RF coil), a receiver, and a RF amplifier for generating RF pulses set at predetermined frequencies. For $^{129}$Xe imaging at 1.5 T field strength, the MRI unit is set to operate in the gas-phase at about 17.6 MHz. The dissolved phase excitation frequency is shifted above the gas phase excitation frequency such as about 196 to at least 200 ppm higher than the gas phase excitation frequency (corresponding to the chemical shift). Thus, the dissolved phase $^{129}$Xe RF excitation frequency can be about 3.52 kHz different from the associated gas-phase excitation frequency. In other embodiments, the imaging method employs a 17.6 MHz gas phase excitation pulse and an associated dissolved phase excitation pulse of about 17.60352 MHz. Of course, the magnet field strength and excitation frequency can vary as is well known to those of skill in the art depending on the target region/tissue or environment undergoing evaluation.

In any event, the RF pulse(s) is transmitted to the patient to excite the nuclei of the polarized $^{129}$Xe. The NMR coil is tuned to a selected frequency range and positioned adjacent to the targeted imaging region to transmit the excitation pulses and to detect responses to the pulse sequence generated by the MRI unit. NMR coils for standard chest imaging can include a wrap-around coil with conductors positioned on both the front and back of the chest. Examples of acceptable coils known to those of skill in the art include a bird-cage configuration, a Helmholtz pair, and a solenoid coil (with field direction perpendicular to the main magnet field). Other NMR coils can be used for other imaging regions of the body (such as the head, torso, and the like).

In certain embodiments, the patient can inhale a quantity of polarized $^{129}$Xe gas into the pulmonary region (i.e., lungs and trachea). After inhalation, the patient can hold his or her breath for a predetermined time such as 5-20 seconds. This can be described as a "breath-hold" delivery. Examples of suitable "single dose" quantities of polarized gases for breath-hold delivery include 0.25-0.5, 0.75, and 1.0-2.0 liters of gas. The dose at inhalation can contain gas with a suitable polarization level, typically so that the polarization at delivery is well above 5%, and preferably a polarization level above about 20%-50%.

In overview, according to embodiments of the instant invention, shortly after inhalation of a suitable amount of hyperpolarized $^{129}$Xe gas (or gas mixture), the MRI unit can deliver a suitable excitation pulse. In particular embodiments, the excitation pulse can be a large flip angle RF excitation pulse to a selected portion of the pulmonary vasculature, although a 90-degree pulse is typically employed. As used herein, "large flip angle" means an angle that is greater than about 30 degrees, and typically greater than about 75 degrees, and more typically about 90 degrees. A 30-degree flip angle will generally yield about 50% as much signal as a 90-degree flip (45 degrees typically giving about 70% as much signal). In certain embodiments, one or a plurality of 90 degree pulses may be applied to destroy all the $^{129}$Xe signal in the tissue and the blood, followed by a rapid train of low flip angle pulses ("low" meaning below 10 degrees, and typically below 3-5 degrees) to monitor the build-up of $^{129}$Xe concentration in tissue and blood after the initial destruction of the signal.

The RF excitation can be selectively performed. That is, that "selective excitation" is generated such that it excites only certain frequencies, i.e., that it excites substantially only the dissolved phase polarized gas. An exemplary delivery of a selective excitation pulse is via a "hard" pulse. As used herein, "hard" pulse includes pulses where the RF is turned on for a short pulse time ("$t_{pulse}$") and then shortly thereafter turned off. In certain embodiments, selective excitation is performed such that the pulse frequency is centered on the dissolved phase resonance desired (i.e., 17.60352 MHz) and has a pulse time, $t_{pulse}$, such that the associated frequency is above the corresponding gas phase excitation frequency (i.e., 17.6 MHz). For example, the frequency spectrum of a square excitation pulse having a time $t_{pulse}$ and which is centered on a frequency ("$f_0$") can be described by the equation:

$$\sin(a(f-f_0))/a(f-f_0), \text{ where } a=3.1416*t_{pulse}. \quad \text{(Equation 3)}$$

Therefore, the pulse time $t_{pulse}$ is preferably set so that the $\sin(a(f-f_0))=0$ for the gas phase component at frequency f. Stated differently, the pulse time $t_{pulse}$ is determined according to the relationship $t_{pulse}=1/(f-f_0)$. In one embodiment, for a 1.5 T magnetic field strength, $f-f_0$ equals 3.52 kHz and $t_{pulse}$ is about 284 μseconds. Of course, as will be recognized by those of skill in the art, alternative approaches can also be used, such as, but not limited to, sinc pulses, gaussian pulses, and the like.

In certain embodiments, a large flip angle pulse is delivered to the target region so as to substantially destroy the incoming $^{129}$Xe polarization or magnetization to set the "0" or monitoring start window for obtaining data at successively longer pulse delay times to analyze the transit time and/or gas exchange dynamics. Thereafter, in certain embodiments, the selective excitation is timed such that it excites the entire pulmonary blood volume. The pulmonary blood volume includes the volume of blood that fills the blood passages associated with the circulatory system between and/or within the lungs and the heart (which can include the volume of blood or a portion of the volume of blood within the boundary lung tissue and/or heart). Advantageously, unlike imaging the gas-phase $^{129}$Xe in the lung where conventionally small flip angles are used to avoid destroying the available magnetization, a large flip angle excitation of the dissolved phase $^{129}$Xe in the pulmonary vasculature allows for the initialization of the "0" level to monitor the gas-exchange dynamics. Further, according to the certain embodiments using inhalation delivery of the $^{129}$Xe, "fresh" magnetization (i.e., polarized $^{129}$Xe) is substantially continuously flowing in from the capillary beds during the procedure. See co-assigned and co-pending U.S. patent application Ser. No. 09/271,476 and U.S. patent application Ser. No. 09/271,476 for descriptions of imaging methods using $^{129}$Xe. The contents of these documents are hereby incorporated by reference as if recited in full herein.

The term "pulmonary and cardiac vasculature" as used herein includes all of the blood vessels within the lungs and/or heart, the chambers of the heart, the passages between the chambers of the heart, as well as the blood vessels between the lungs and heart, and blood vessels between the lungs or heart and other tissues and/or organs. The pulmonary and cardiac vasculature includes, but is not limited to, the pulmonary veins and arteries and associated capillaries, the left and right atria of the heart, the left and right ventricles of the heart, the myocardium, the aorta and aortic arch, the coronary artery, the coronary arteries, the subclavian arteries, and the carotid arteries.

In operation, almost immediately upon inhalation of hyperpolarized $^{129}$Xe into the lungs, Xe begins to dissolve into the pulmonary blood stream (typically in under about 100 ms). The concentration of Xe in the pulmonary capillary beds ("$[Xe]_p$", can be assumed to equilibrate after an initial gas transit time (as the gas travels across the alveolar-capillary membrane) with the concentration of Xe in the lung gas spaces ("$[Xe]_L$"). Thus, the relationship can be stated as:

$$[Xe]_P = 8[Xe]_L, \quad \text{(Equation 4)}$$

where "8" is the solubility coefficient, such as the Xe blood/gas partition coefficient or blood solubility. This concentration can be expected to equilibrate in the venous side of the pulmonary vasculature just a few seconds after inhalation. One of skill in the art can select a suitable solubility coefficient(s) for a particular application and compartment(s) under evaluation. The standard unit for concentration is an "amagat" which refers to 1 atmosphere of gas pressure at a temperature of 273K. For humans whose lungs contain one atmosphere of gas and whose temperature is about 310K, all gas densities should be scaled down by a factor of about A=0.88 amagat per atmosphere. For a patient inhaling a volume ("$V_{Xe}$") of Xe into their lungs of volume ("$V_L$"), the resulting Xe density in the lung $[Xe]_L$ will be $$[Xe]_L = A\frac{V_{Xe}}{V_L}. \quad \text{(Equation 5)}$$

Thus, the concentration of Xe in the pulmonary blood $[Xe]_P$ will be related to the inhaled gas volume $V_{Xe}$, and can be stated by the expression:

$$[Xe]_P = \lambda A\frac{V_{Xe}}{V_L}. \quad \text{(Equation 6)}$$

For reference, an estimate of λ for Xe in blood is that 8≈0.15. Other coefficient values may be used as appropriate. For example, λ in tissue (typically the tissue between the alveoli and the capillaries) may be about 0.10, a typical value of the tissue-blood partition may be about 0.75.

As an example, a patient who inhales 1 L of Xe into his 6 L lung will yield a Xe density in the lungs of $[Xe]_L \approx 0.15$ amagat, and correspondingly a Xe density in the pulmonary capillary beds of $[Xe]_P \approx 0.02$ amagat. Thus, the dissolved polarized $^{129}$Xe gas in the pulmonary capillary beds will substantially saturate at approximately ⅙ the concentration of the lung gas.

As described above and in co-pending U.S. patent application Ser. No. 09/271,476, a patient who inhales 1 L of Xe into the lungs (having about a 6 L lung volume) will yield about or dissolve into or saturate at about ⅙ of that value of the xenon concentration (0.02 amagat) in the pulmonary vasculature and associated blood. For additional description of signal compensation or adjustment, signal per voxel, and perfusion images, see U.S. patent application Ser. No. 09/271,476, the contents of which are hereby incorporated by reference as if recited in full herein. In certain embodiments, the method uses frequency selective large angle RF excitation pulses "α" (preferably 90° pulses) that substantially deplete the $^{129}$Xe in the pulmonary blood but leaves the hyperpolarized gas in the lungs substantially undisturbed to define the initial monitoring period during which dynamic NMR signal data is obtained. In this embodiment, the repetition time interval between RF pulses ($T_R$) and the pulmonary blood flow rate (F) can be used to determine the effective pulmonary volume ($V_{eff}$) containing (dissolved phase) hyperpolarized $^{129}$Xe. This relationship assumes that $T_R$ is less than or substantially equal to the time it takes for the polarized $^{129}$Xe to leave the pulmonary blood ($t_p$). As discussed above, for typical blood flow rate and estimated volume of venous pulmonary blood, $t_p$ is approximately 2.5 seconds. Thus, with a large RF excitation pulse "α" (i.e. α=90°), the dissolved pulmonary $^{129}$Xe signal strength in the pulmonary blood (the linear portion of the pulmonary uptake curve) is proportional to the product of coil gain ("G"), Xe polarization ("$P_{xe}$"), and polarized Xe density or concentration in the vasculature ($[Xe]_p = \lambda [Xe]_L$), which can be stated by the following expression:

$$S_P(T_R) = GP_{Xe}\delta[Xe]_L F T_R.$$ Equation (7)

Notably, the signal strength is dependent on both the pulse interval ($T_R$) and the blood flow rate (F), and in the limit of between about 0.5 sec<$T_R$<2.5, it is reasonable to consider the build-up of Xe blood signal to be a linear function as described by equation (7). The dissolved signal intensity versus repetition time will have an associated slope which can be mathematically expressed as follows:

$$\frac{dS_P}{dT_R} = GP_{Xe}\lambda[Xe]_L F.$$ Equation (8)

The slope of the $^{129}$Xe NMR uptake curve in the pulmonary blood is directly proportional to the pulmonary blood flow rate (F). Calibration of the blood flow rate is obtainable by evaluating the gas phase signal ("$S_L$") in the lung, the signal having an associated small RF tipping angle (excitation angle) ("$\alpha_L$"). The gas phase signal can be expressed by the equation:

$$S_L = GP_{Xe}[Xe]_L V_L \sin \alpha_L.$$ Equation (9)

The pulmonary blood flow rate (F) can be stated by the ratio of the hyperpolarized $^{129}$Xe gas and dissolved phase signals. This ratio cancels receiver gain (G) and polarization value $P_{xe}$. Accordingly, the (ventilated) blood flow rate (F) can be expressed by the following:

$$F = \frac{V_L \sin \alpha_L (dS_P/dT_R)}{\lambda S_L}.$$ Equation (10)

Advantageously, with measurements of the Xe/blood partition coefficient (λ) and the total lung volume ($V_L$), a quantitative measurement of blood flow is established according to a method of the instant invention. As will be appreciated by one of skill in the art, lung volume can be easily established to about 20% accuracy with techniques known to those of skill in the art, such as, but not limited to, spirometry. In addition, lung volume may also be measured using polarized $^{129}$Xe and/or $^3$He MRI.

The spectroscopic evaluation methods do not require a polarization calibration because the measurement can be "self-calibrating." Stated differently, the polarization can be cancelled by comparing dissolved and gaseous xenon signal, both of which can be assumed to have substantially the same or identical polarization to the extent that T1 relaxation in the blood can be negligible and is reasonable to ignore because the T1 of Xenon in the blood has been measured to be between 5-6 seconds, and the pulse interval timing and/or evaluation time is substantially below 5-6 seconds (typically between 0.5-2.5 seconds as noted above).

The present invention has been described above with respect to particular preferred embodiments. Those skilled in the art, however, will appreciate that the invention can be employed for a broad range of applications. Methods for imaging or obtaining information about gas exchange barriers, physiologic function and dynamic functional evaluation of systems, membranes, biostructures or environments and/or perfusion mapping using dissolved hyperpolarized $^{129}$Xe may be carried out according to the present invention using magnetic resonance or spectroscopic techniques known to those skilled in the art and/or the methods described herein. See, e.g., U.S. Pat. No. 5,833,947; U.S. Pat. No. 5,522,390; U.S. Pat. No. 5,509,412; U.S. Pat. No. 5,494,655, U.S. Pat. No. 5,352,979; and U.S. Pat. No. 5,190,744. See also Hou et al., *Optimization of Fast Acquisition Methods for Whole-Brain Relative Cerebral Blood Volume (rCBV) Mapping with Susceptibility Contrast Agents*, 9 J. Magnetic Resonance Imaging 233 (1999); Simonsen et al., *CBF and CBV Measurements by USPIO Bolus Tracking: Reproducibility and Comparison with Gd-Based Values*, 9 J. Magnetic Resonance Imaging 342 (1999); Mugler III et al., *MR Imaging and Spectroscopy Using Hyperpolarized $^{129}$Xe gas: Preliminary Human Results*, 37 Magnetic Resonance in Medicine, pp. 809-815 (1997); Belliveau et al., *Functional Cerebral Imaging by Susceptibility-Contrast NMR*, 14 Magnetic Resonance in Medicine 14 538 (1990); Detre et al., *Measurement of Regional Cerebral Blood Flow in Cat Brain Using Intracarotid $^2$H$_2$O and $^2$H NMR Imaging*, 14 Magnetic Resonance in Medicine 389 (1990); Frank et al., *Dynamic Dysprosium-DTPA-BMA Enhanced MRI of the Occipital Cortex; Functional Imaging in Visually Impaired Monkeys by PET and MRI* (Abstract), Ninth Annual Scientific Meeting and Exhibition of the Society of Magnetic Resonance In Medicine (Aug. 18-24, 1990); Le Bihan, *Magnetic Resonance Imaging of Perfusion*, 14 Magnetic Resonance in Medicine 283 (1990); and Rosen et al., *Perfusion Imaging by Nuclear Magnetic Resonance*, 5 Magnetic Resonance Quarterly 263 (1989). The contents of these documents are hereby incorporated by reference as if recited in full herein.

In particular embodiments, the present invention can be practiced to give a quantitative assessment of perfusion which can be used to evaluate systemic function as will be appreciated by one of skill in the art. According to this embodiment, signal intensity can be followed over time as noted above. Examples of such quantitative relationships, which have been developed for use with radioactive contrast agents, may be particularly suitable for dissolved phase $^{129}$Xe MR imaging and spectroscopy. See, generally, Lassen, *Cerebral Transit of* an *Intravascular Tracer may Allow Measurement of regional Blood Volume but not Regional Blood Flow,* 4 J. Cereb. Blood Flow and Metab. 633 (1984).

Furthermore, the inventive methods may be used for wide range of diagnostic and evaluative applications, preferably those related to cardiac, pulmonary or cardiovascular function, as described in more detail herein.

Other applications of the present invention include, but are not limited to: identification and assessment of the presence or absence and/or severity of cardiac ischemias and/or infarcts; localization and assessment of thrombi and plaques; determination of "therapeutic windows" for administering heparin, vasodilators, antihypertensive agents, calcium antagonists and the like, e.g., in reversible focal ischemia; monitoring of other induced vasodilator effects; detection and quantitative evaluation of the severity of ischemias; monitoring the vasodilatory or vasocontractory effects of a physiologically active substance; and monitoring surgically induced blood perfusion variations.

Many researchers have investigated characteristic chemical shifts observed when hyperpolarized $^{129}$Xe comes into contact with different tissues, as seen in Table 1. As shown, large frequency shifts (on the order of 200 parts per million or "ppm") from free gas phase (referenced at 0 ppm) have been observed. This frequency shift is far greater than that observed with proton spectroscopy (generally stated, at most about 5 ppm). Therefore, spectroscopy is a modality which may be particularly suited to capitalize upon the behavior of hyperpolarized $^{129}$Xe.

TABLE 1

Characteristic shifts from free gaseous hyperpolarized $^{129}$Xe (referenced at 0 ppm) of hyperpolarized $^{129}$Xe when exposed to different tissues.

| Tissue | Ppm | Reference |
|---|---|---|
| Water | 191.2 | Wilson 99 |
| Epicardial fat | 192 | Swanson 99 |
| Brain, lipid rich | 194 | Albert 99 |
| Brain tissue | 194.5 | Swanson 97 |
| Plasma | 195.6 | Wilson 99 |
| Brain | 198.0 | Wilson 99 |
| Lung parenchyma | 198.6 | Wilson 99 |
| Brain tissue | 199 | Swanson 99 |
| Kidney | 199.8 | Wilson 99 |
| Brain - lipid poor | 201 | Albert 99 |
| Liver | 201.8 | Wilson 99 |
| *T. Californica* membrane | 209 | Miller 81 |
| RBC (oxygenated) | 213.0 | Wilson 99 |
| RBC (de-oxygenated) | 216.0 | Albert 99 |

As discussed hereinabove, hyperpolarized $^{129}$Xe can be administered to a patient by inhalation or injection. If the administration modality is injection, $^{129}$Xe can be suspended in a carrier fluid or injected directly such as in gaseous form. However, regardless of what tissue is of interest, if the $^{129}$Xe is suspended in a carrier fluid, the carrier fluid itself may distort the results of the spectra and/or substantially obscure a spectral peak of interest which may thereby cause the chemical shift of hyperpolarized $^{129}$Xe to differ from that which would be observed with merely the tissue of interest and hyperpolarized $^{129}$Xe. Therefore, direct injection of gaseous $^{129}$Xe or administration via inhalation may be particularly suitable for certain embodiments or applications. For additional discussion of direct injection of gaseous $^{129}$Xe, see co-pending U.S. application Ser. No. 09/804,369, the contents of which are hereby incorporated by reference as if recited in full herein.

In certain embodiments, the spectral peaks may be quantified by normalizing the spectral data. The term "normalizing" means to mathematically adjust the obtained dissolved $^{129}$Xe NMR signal data of the spectral peak or peaks of interest using predetermined adjustment or scaling factors, relationships, or mathematical equations to account for selected signal variables (such as polarization strength, dose, polarization concentration/blend in the dose, and the like). This adjustment may include taking the mathematic ratio of the values of certain peaks associated with selected known biomatter (RBC, plasma, etc.) within the response spectrum to the tissue, blood, or gas signals to quantify the hyperpolarized gas signal in the region of interest. The adjustment may include computing a numerical value of the signal strength obtained by factoring it to the polarization level (and/or quantity) of the administered gas that can be measured at the time of delivery to obtain a base or reference spectrum to quantify the magnitude of the signal. The normalization can be carried out using the polarization strength of the gas as it is delivered to the patient and may also adjust the obtained signal value for the amount of polarized gas (% blend of polarized gas) administered thereto to account for intensity variation caused by the % of polarized gas administered and/or the polarization level of the gas.

A region-specific NMR coil can be positioned over the region of interest and to transmit a selected RF pulse sequence. The coil receives a FID signal. Localizing gradients can also be applied about the region of interest so as to localize the resonance region. For example, localizing gradients can be applied so that a desired region of interest is excited. In any event, the Fourier Transform of the acquired data is then calculated. The transformed signal data can be further processed, which processing may include, but is not limited to, one or more of subtracting background noise, filtering undesirable signal data (such as those portions of the signal or spectra attributed to carrier liquids or deposits in non-target tissue or blood and the like), determining the frequency shift for any number of peaks within pre-determined ranges in the spectrum, and normalizing the data such as finding the ratios between magnitudes and/or areas of different spectral peaks within the response spectrum or accounting for polarization level and amount of polarized gas delivered to the subject. For further discussion of exemplary background subtraction or adjustment methods and cardiac gating methods, see co-pending U.S. application Ser. Nos. 09/271,476 and 09/271,476 incorporated by reference hereinabove.

The present invention finds use for both pre-clinical animal studies, veterinary and medical applications. The present invention may be advantageously employed for diagnostic evaluation and/or to monitor the treatment of subjects, in particular human subjects, because it is minimally invasive and may be safer (e.g., less toxic) than other methods known in the art (e.g., radioactive methods). In general, the inventive methods may be more readily accepted because they avoid radioactivity or toxic levels of chemicals or other agents. Subjects according to the present invention can be any animal subject, and are preferably mammalian subjects (e.g., humans, canines, felines, bovines, caprines, ovines, equines, rodents, porcines, and/or lagomorphs), and more preferably are human subjects.

The present invention is described with reference to flowchart illustrations and/or block diagrams of methods, and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, embedded processor or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

As will be appreciated by one of skill in the art, the present invention may be embodied as a method, data or signal processing system, or computer program product. Accordingly, the present invention may take the form of an entirely software embodiment or an embodiment combining software and hardware aspects. Furthermore, the present invention may take the form of a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java7, Smalltalk or C++. However, the computer program code for carrying out operations of the present invention may also be written in conventional procedural programming languages, such as the "C" programming language or even assembly language. The program code may execute entirely on the user's computer, partly on the user's computer, as a stand-alone software package, partly on the user=s computer and partly on a remote computer or entirely on the remote computer. In the latter scenario, the remote computer may be connected to the user=s computer through a local area network (LAN) or a wide area network (WAN), or the connection may be made to an external computer (for example, through the Internet using an Internet Service Provider).

The flowcharts and block diagrams used herein illustrate systems and/or operations that can be used to obtain dynamic NMR signal data and analyze and evaluate the data to assess selected parameters associated with lung physiology or respiratory and/or cardiopulmonary function or disorders according to embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Figure 14:
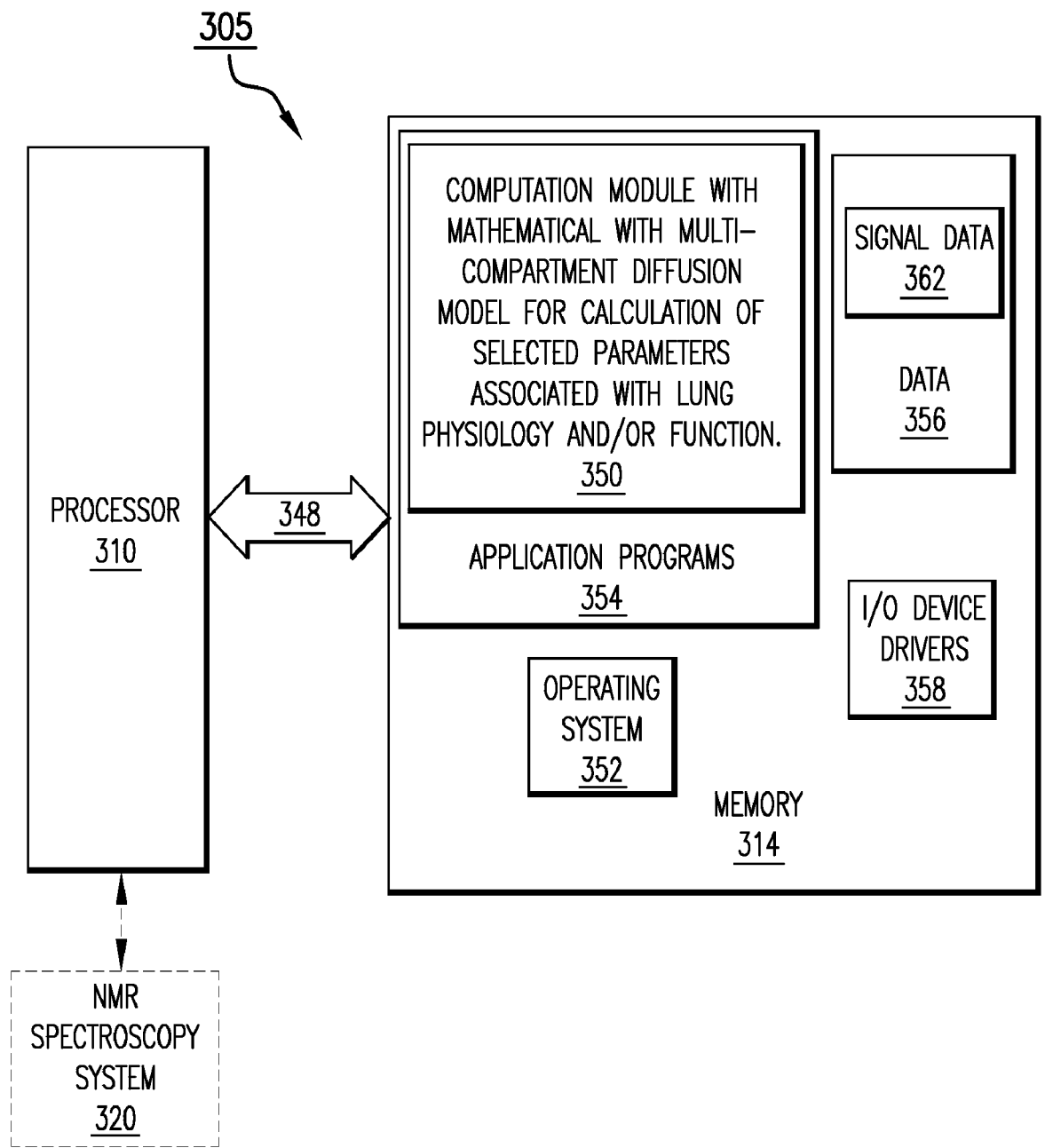
FIG. 14 is a schematic illustration of a system suitable for calculating measurement values of selected parameters associated with lung physiology and/or function according to embodiments of the present invention.

FIG. 14 is a block diagram of exemplary embodiments of data processing systems that illustrates systems, methods, and computer program products in accordance with embodiments of the present invention. The processor 310 communicates with the memory 314 via an address/data bus 348. The processor 310 can be any commercially available or custom microprocessor. The memory 314 is representative of the overall hierarchy of memory devices containing the software and data used to implement the functionality of the data processing system 305. The memory 314 can include, but is not limited to, the following types of devices: cache, ROM, PROM, EPROM, EEPROM, flash memory, SRAM, and DRAM.

As shown in FIG. 14, the memory 314 may include several categories of software and data used in the data processing system 305: the operating system 352; the application programs 354; the input/output (I/O) device drivers 358; a computation module 350; and the data 356. The computation module 350 includes a mathematical diffusion model of gas exchange using multiple compartments. The computation module 350 is used to calculate selected parameters associated with lung physiology by quantifying predetermined constituents of the NMR signal build-up or uptake curves of the polarized $^{129}$Xe in multiple compartments (gas or alveolar space, tissue, and capillary or blood). Data associated with the uptake curves can be used to determine the thickness of the membrane. The slopes, and/or intercepts of the asymptotes of the build-up curves can also be calculated and used to determine or measure function and/or physiology.

In certain embodiments, the computation module 350 includes equations for calculating at least one, typically at least two, and, in certain embodiments, all of the following parameters: total diffusion length, tissue thickness, blood or capillary compartment thickness, perfusion, mean transit time, relative blood volume, hematocrit, and alveolar radius. In certain embodiments, the multiple parameters can be calculated using a common data set obtained in a single session. The computation module 350 can also mathematically take the ratio between the uptake time constant and the mean transit time to indicate whether the gas exchange is perfusion or diffusion limited. The computation module 350 may also calculate the total diffusion length using the uptake time constant (the diffusion length is proportional to the square root of the time constant as noted in Equation 18) and/or the membrane thickness (typically using multiple signal parameters in multiple compartments as defined in Equation 21A).

The computation module 350 can be used to assess therapeutic response or disease progression of a thickening or thinning of the alveolar membrane.

The computation module 350 may be configured to assess the data to determine whether one or more physiological abnormalities are present in order to assess the likelihood that the patient has a drug-induced or environmentally-induced lung injury or other lung abnormality or disorder. As the lung reacts to toxicity or trauma, one or more of the selected parameters as a sensitive probe to assess whether a transplant recipient (of a lung, heart, kidney, liver, or other organ) is undergoing a bio-rejection response to the transplant. The computation module 350 may be directed to assess a subject's physiological response to a therapeutic drug for known problematic drugs (chemotherapeutic agents) or for drug discovery or clinical trials and the like to provide data that can inhibit the progression of lung injury.

The data 356 may include signal (constituent and/or composite spectrum lineshape) data 362 which may be obtained directly from a NMR spectroscopy system or data or signal acquisition system 320. As will be appreciated by those of skill in the art, the operating system 352 may be any operating system suitable for use with a data processing system, such as OS/2, AIX or OS/390 from International Business Machines Corporation, Armonk, N.Y., WindowsCE, WindowsNT, Windows95, Windows98, Windows2000, WindowsXP or Windows XT from Microsoft Corporation, Redmond, Wash., PalmOS from Palm, Inc., MacOS from Apple Computer, UNIX, FreeBSD, or Linux, proprietary operating systems or dedicated operating systems, for example, for embedded data processing systems.

The I/O device drivers 358 typically include software routines accessed through the operating system 352 by the application programs 354 to communicate with devices such as I/O data port(s), data storage 356 and certain memory 314 components and/or the image acquisition system 320. The application programs 354 are illustrative of the programs that implement the various features of the data processing system 305 and preferably include at least one application that supports operations according to embodiments of the present invention. Finally, the data 356 represents the static and dynamic data used by the application programs 354, the operating system 352, the I/O device drivers 358, and other software programs that may reside in the memory 314.

While the present invention is illustrated, for example, with reference to the computation module 350 being an application program in FIG. 14, as will be appreciated by those of skill in the art, other configurations may also be utilized while still benefiting from the teachings of the present invention. For example, the module 350 may also be incorporated into the operating system 352, the I/O device drivers 358 or other such logical division of the data processing system 305. Thus, the present invention should not be construed as limited to the configuration of FIG. 14, which is intended to encompass any configuration capable of carrying out the operations described herein.

The I/O data port can be used to transfer information between the data processing system 305 and the system 320 or another computer system or a network (e.g., the Internet) or to other devices controlled by the processor. These components may be conventional components such as those used in many conventional data processing systems, which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 14 but is intended to encompass any configuration capable of carrying out the operations described herein.

Particular embodiments of the invention will now be described in the following non-limiting examples.

EXAMPLES

The ability to quantify pulmonary diffusing capacity and perfusion using dynamic hyperpolarized $^{129}$Xe NMR spectroscopy was experimentally demonstrated. A model of alveolar gas exchange was developed, which, in conjunction with $^{129}$Xe NMR, allows quantification of average alveolar wall thickness, pulmonary perfusion, capillary diffusion length and mean transit time. The technique was employed to compare a group of naïve rats (n=10) with a group of rats with acute inflammatory lung injury (n=10), caused by instillation of lipopolysaccharide (LPS). The measured structural and perfusion-related parameters were in agreement with reported values from studies using non-NMR methods. Significant differences were found between the groups were found in total diffusion length (control 8.6±µm, LPS 10.0±0.8 µm, p<0.001) and in average alveolar wall thickness (control 4.9±0.9 µm, LPS 6.4±1.2 µm, p<0.01), whereas no statistically significant differences were observed in the perfusion-related parameters. These results demonstrate the ability of the methods and operations contemplated by embodiments of the present invention to distinguish two main aspects of lung function, namely diffusing capacity and pulmonary perfusion.

In the description that follows, alternative and/or supplemental calculation models and equations relative to the equations and descriptions presented above, will be described that can be used to determine selected parameters associated with lung physiology and/or function using polarized $^{129}$Xe NMR signal data. The time constant "τ" can be the time constant of any uptake curve obtained. It may also represent an uptake curve associated with a selected combination of compartments, such as the tissue and capillary (blood) compartments.

Figure 7:
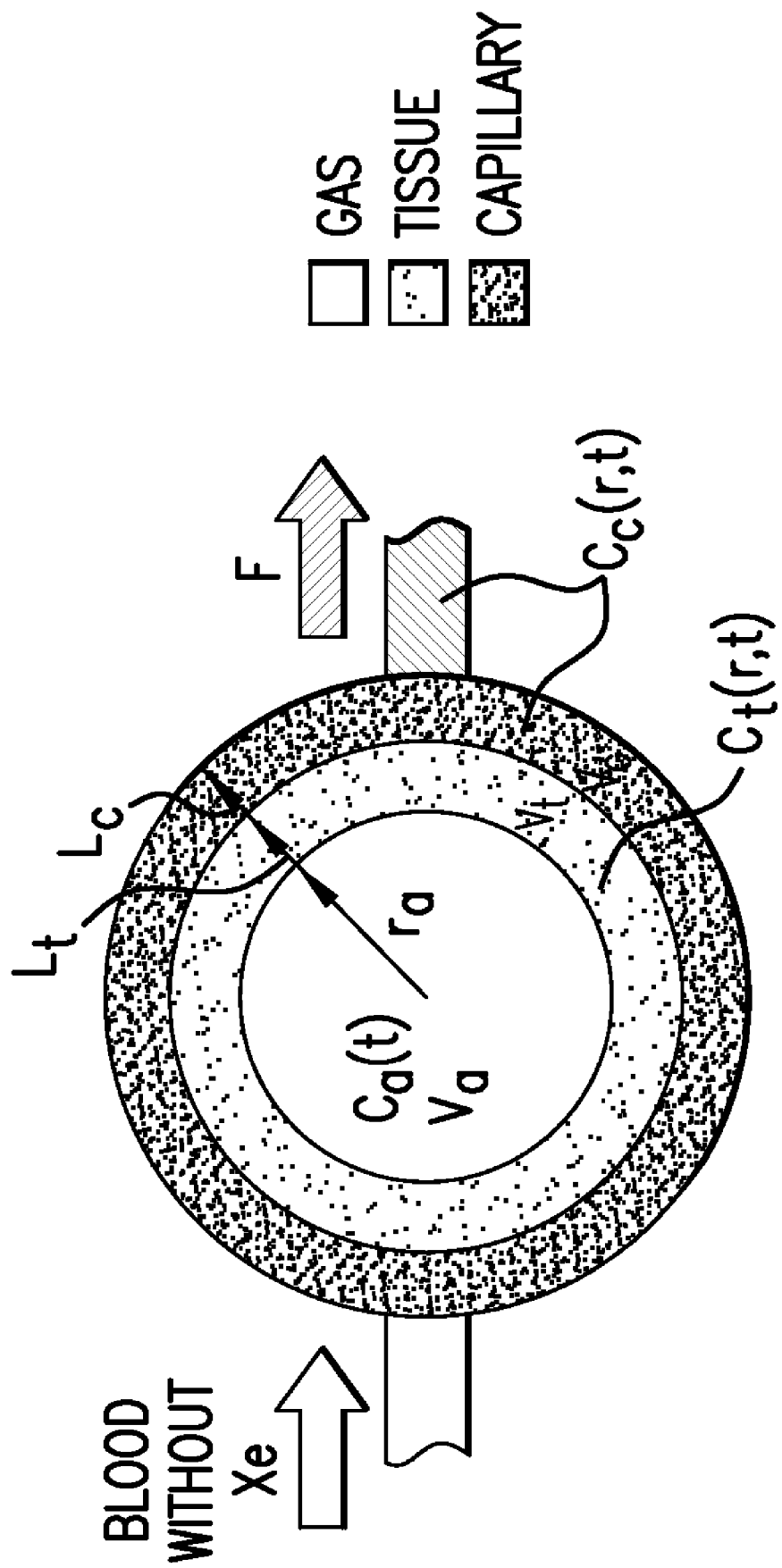
FIG. 7 is a schematic of an alveolus diffusion model illustrating multiple compartments associated with gas exchange.

Referring to FIG. 7, the uptake of polarized $^{129}$Xe from the alveoli or alveolar gas space to the blood can be modeled with a three-compartment model with spherical symmetry as shown. In this single-alveolar model, xenon diffuses into the alveolus through a tissue compartment with thickness $L_t$. After passing the tissue compartment, the xenon diffuses an average distance $L_c$, within a capillary compartment, including plasma and red blood cells. Finally, the xenon is transported away from the capillary compartment with a flow F. Since the alveolar radius, $r_a$, is an order of magnitude larger than the thickness of the tissue and capillary layers, the spherical symmetry model may however simplify to a 1-dimensional model, described by Fick's law (Equation 11) as described, for example, in Dowse et al., *The estimation of the diffusion constant and solubility of O(2) in tissue using kinetics*, J Theor Biol, 2000; 207:531-541; the contents of which are hereby incorporated by reference as if recited in full herein. The diffusion equation can be represented by the following expression:

$$D\frac{\partial^2 C(r,t)}{\partial r^2} - \frac{\partial C(r,t)}{\partial t} = 0 \qquad \text{Equation (11)}$$

The diffusion coefficient, D, of xenon can be assumed equal in the tissue and the capillary, with a value of approx. $1 \cdot 10^{-9}$ m²/s. See Wolber et al., *Diffusion of hyperpolarized $^{129}$Xe in biological systems: effect of chemical exchange*, In Proc 8th Annual Meeting ISMRM, Denver, 2000, p. 754; the contents of which is hereby incorporated by reference as if recited in full herein. The boundary conditions to Equation 11 are given by the mass-transport laws across the compartment surfaces and the respective solubility for xenon:

$$\left. \begin{array}{l} C_t(r_a, t) = \lambda_T C_a(t) \\ A_a D \dfrac{\partial C_t(r_a, t)}{\partial r} = V_d \dfrac{\partial C_a(t)}{\partial t} \end{array} \right\} \text{(alveol-tissue boundary)} \quad \text{Equation (12A)}$$

$$\left. \begin{array}{l} \lambda_P C_c(r_1, t) = C_t(r_1, t) \\ \dfrac{\partial C_c(r_1, t)}{\partial r} = \dfrac{\partial C_t(r_1, t)}{\partial r} \end{array} \right\} \text{(tissue-capillary boundary)} \quad \text{Equation (12B)}$$

$$A_a D \dfrac{\partial C_c(r_2, t)}{\partial r} = -F C_c(r_2, t) \quad \text{Equation (12C)}$$

(outer capillary boundary)

where $r_1 = r_a + L_t$, $r_2 = r_1 + L_c$, $A_a = 4\pi r_a^2$, $V_a = \frac{4}{3}\pi r_a^3$ where $C_a$, $C_t$ and $C_c$ denote the concentrations in the alveolar, tissue and blood compartments, respectively. $\lambda_T$ is the Ostwald solubility coefficient in tissue, and $\lambda_p$ is the tissue-blood partition coefficient. Based on reported measurements of xenon solubility in various tissues, values of $\lambda_T = 0.10$ and $\lambda_p = 0.75$ were used in this evaluation of the diffusion model.

Figure 8:
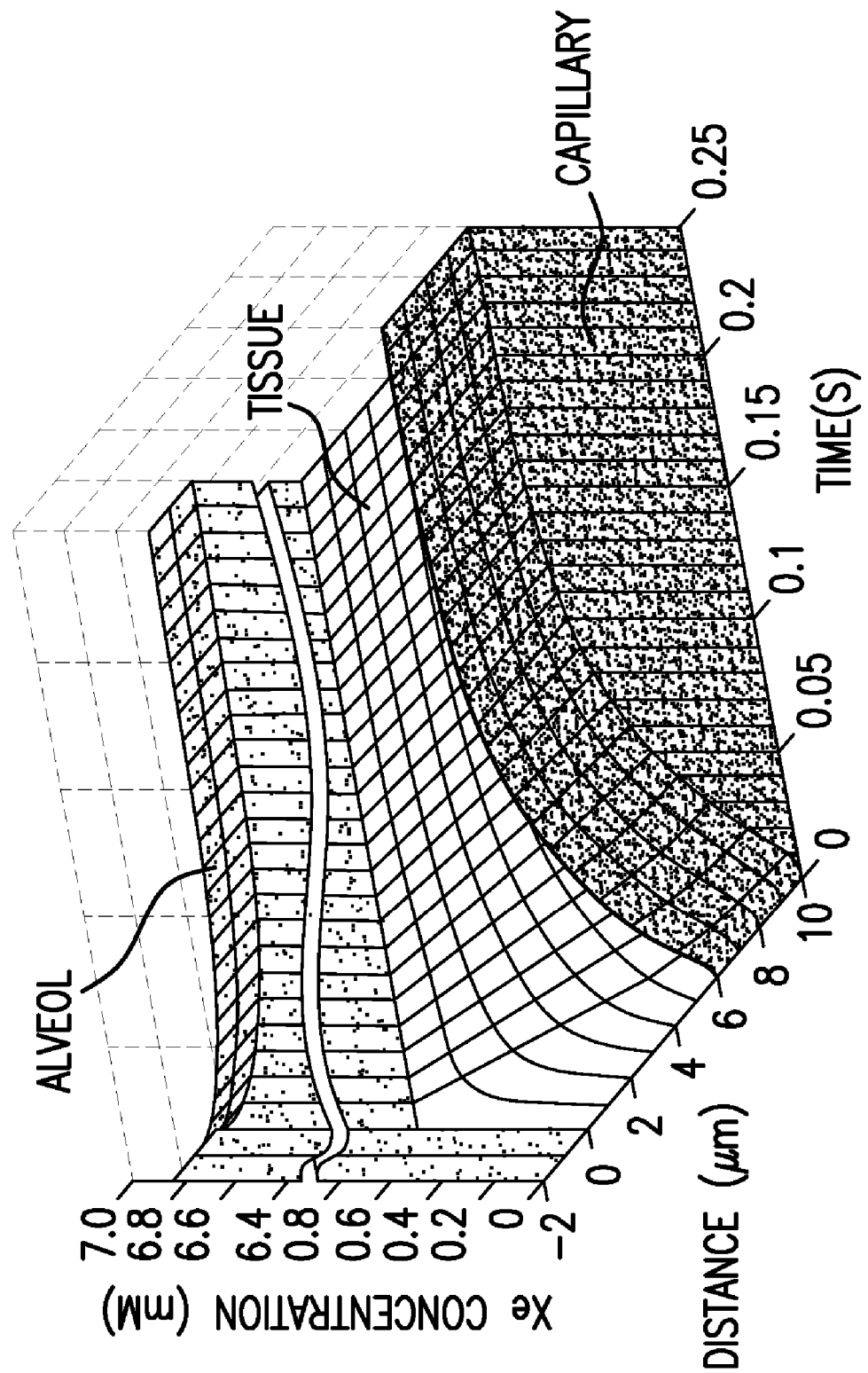
FIG. 8 is a graph of xenon concentration (mM) versus distance (μm) over time of the numerical solution of a partial differential equation representing the xenon concentration in the alveoli, tissue and capillary compartments, according to embodiments of the present invention.

A numerical solution of Equation 11 with the boundary conditions given by Equations 12A-12C is shown in FIG. 8. That is, FIG. 8 illustrates the numerical solution of partial differential Equation 11, graphed in distance (in μm) versus $^{129}$Xe concentration (in mM) over time in the alveoli (gas), tissue, and capillary (blood) compartments.

When $\lambda_p$ is near unity, the calculations can be simplified by ignoring the boundary conditions at the tissue-capillary surface and treating the tissue and capillary compartments as a single compartment with concentration $C(r,t)$ and thickness $L = L_t + L_c$. The condition at the outer boundary as described in Equation 12C can be replaced with the following mathematical expression:

$$\lambda_P A_a D \dfrac{\partial C(r_2, t)}{\partial r} = -F C(r_2, t) \quad \text{Equation (13)}$$

This simplification will still yield the exact solution if $\lambda_p = 1$, and the error is small if the value of $\lambda_p$ is relatively close to 1. A transformation of variables can be carried out according to $\tilde{r} = \pi/L\,(r - r_a)$, $0 < \tilde{r} \leq \pi$ and $\tilde{t} = D(\pi/L)^2 t$, $\tilde{t} \geq 0$. After the transformation of variables, Equation 11 has the general solution $$C(\tilde{r}, \tilde{t}) = \exp(-\chi^2 \tilde{t})\,(A \sin(\chi \tilde{r}) + B \cos(\chi \tilde{r})) \quad \text{Equation (14)}$$

Applying the conditions at the inner and outer boundaries ($\tilde{r} = 0$ and $\tilde{r} = \pi$) to Equation 14 yields that $\chi$ can satisfy the equation:

$$L r_a (12\pi r_a D \lambda_P \lambda_T + F)\pi \chi \tan(\pi \chi) + 4\pi D r_a^3 \lambda_p (\pi \chi)^2 - 3 F L^2 \lambda_t = 0 \quad \text{Equation (15)}$$

Since Equation 15 has an infinite number of roots $\chi_0$, $\chi_1$, $\chi_2$, ..., the full solution to Equation 11 can be expressed as the linear combination:

$$C(\tilde{r}, \tilde{t}) = \sum_{n=0}^{\infty} \varphi_n \exp(-\chi_n^2 \tilde{t})(A \sin(\chi_n \tilde{r}) + B \cos(\chi_n \tilde{r})) \quad \text{Equation (16)}$$

$$\chi_0 < \chi_1 < \chi_2 < \ldots$$

where the coefficients $\phi_n$ are chosen such that the initial condition at $\tilde{t} = 0$ is fulfilled. The longest time constant $(1/\chi_0^2)$ depends mainly on the alveolar radius, $r_a$, and the blood flow, F, and can be shown to be of the order of minutes, i.e., about two magnitudes longer than the time-scale of the measurement. The remaining roots $\chi_1, \chi_2, \ldots$ represent the transients occurring before equilibration of the concentration. Without flow (i.e. if F=0), Equation 15 simplifies to:

$$\dfrac{r_a}{L}\pi \chi + 3\lambda_T \tan(\pi \chi) = 0 \quad \text{Equation (17)}$$

If $r_a/L \gg 1$, the roots are approximately $\chi_1 \approx \frac{1}{2}$, $\chi_2 \approx \frac{3}{2}$, $\chi_3 \approx \frac{5}{2}$, .... The exponential terms $\exp(-\chi_n^2 \tilde{t})$ will thus, after transformation to the original variables r and t, correspond to exponential terms $\exp(-t/\tau_n)$, with $\tau_n^{-1} = \chi_n^2 D(\pi/L)^2$. Because the time constant $\tau_1$ can be determined experimentally with the NMR data, it follows that the total thickness of the tissue and capillary compartments can be estimated according to:

$$L \approx \dfrac{\pi}{2}\sqrt{D\tau_1} \quad \text{Equation (18)}$$

By comparing with a direct, numerical solution of Equation 11, the error in the L value estimated from Equation 18 is less than about 10% for a wide range of pulmonary blood flows.

Figure 9:
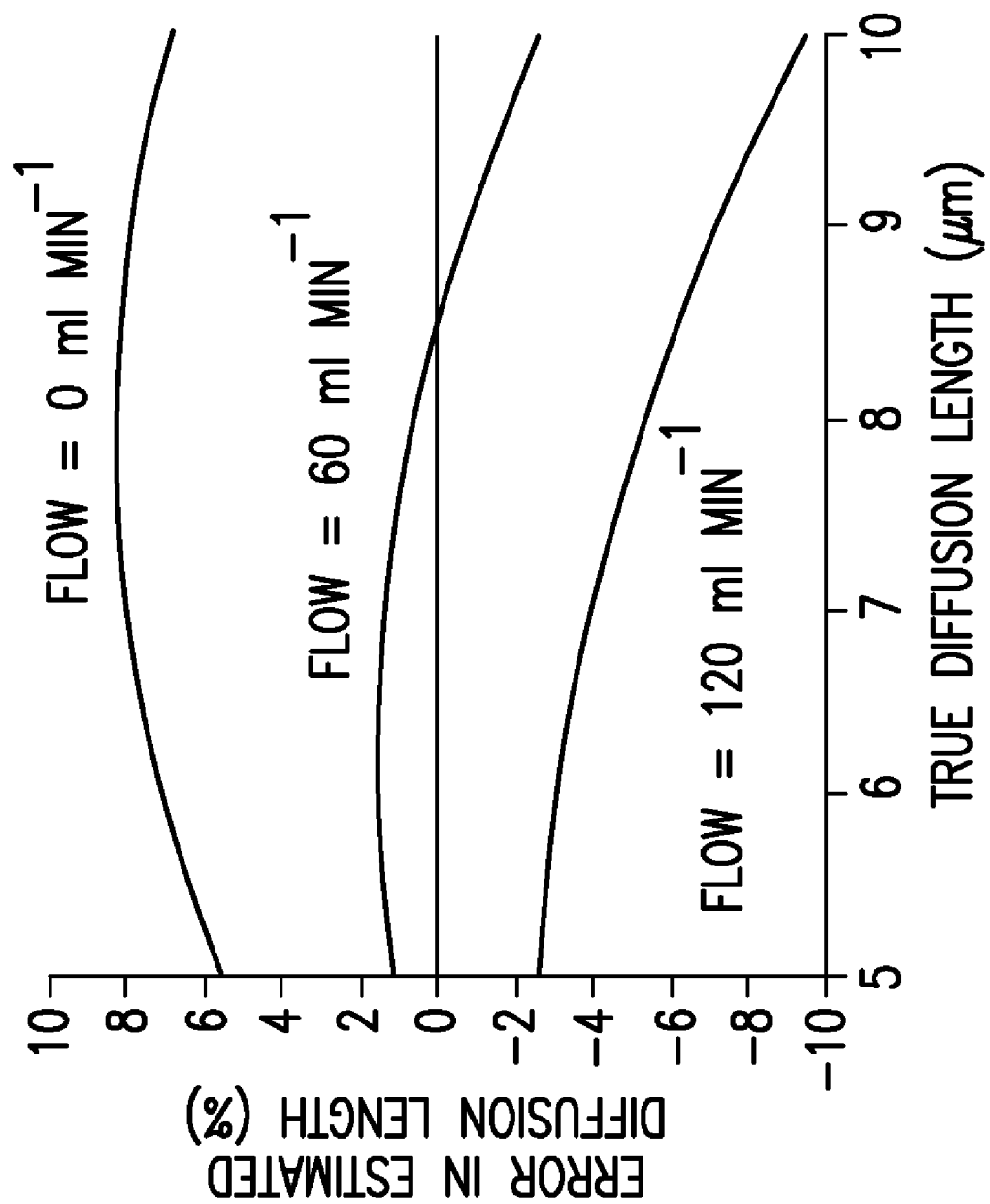
FIG. 9 is a graph of error in estimated diffusion length using an uptake time constant and a mathematical relationship for varying diffusion lengths and pulmonary blood flows according to embodiments of the present invention.

FIG. 9 is a graph of the error in the estimated diffusion length (in %) versus true diffusion length (μm) for three different flow rates: 0 ml/min, 60 ml/min, and 120 ml/min when using relationship expressed by Equation 18. For varying diffusion lengths and pulmonary blood flows, the estimated diffusion length "L" was calculated according to Equation 18 using the true time constant $\tau_1$ as determined by Equation 11. The total pulmonary blood flow was equally distributed across a total of about $1 \times 10^6$ alveoli.

The xenon in the capillary (or blood) compartment can be divided in a fraction H inside the red blood cells, and a fraction (1−H) dissolved in the plasma, where H denotes the hematocrit. After the transient buildup, the concentrations in tissue, plasma and red blood cells can be considered independent of the r- and t-coordinates and proportional to the respective Ostwald solubility: $C_t = \alpha \lambda_T$, $C_{pl} = \alpha \lambda_{pl}$, $C_{RBC} = \alpha \lambda_{RBC}$.

The NMR signals coming from tissue, plasma and red blood cells can then be expressed as:

$$S_{tissue}(t) = \alpha \lambda_T A_a L_t \quad \text{Equation (19A)}$$

$$S_{plasma}(t) = \alpha \lambda_{pl} A_a L_c (1 - H) + \int_0^t (1 - H) F \alpha \lambda_{pl} d\tau \quad \text{Equation (19B)}$$

$$S_{RBC}(t) = \alpha \lambda_{RBC} A_a L_c H + \int_0^t H F \alpha \lambda_{RBC} d\tau \quad \text{Equation (19C)}$$

The integral terms in Equations 19B and 19C correspond to polarized $^{129}$Xe that has left the capillary compartment surrounding the alveolus, but still generates signal contribution downstream of the alveolus.

The signal $S_{RBC}$ gives rise to a separate spectral peak, whereas the positions of $S_{tissue}$ and $S_{plasma}$ coincide. See e.g., Wolber et al., Hyperpolarized $^{129}$Xe NMR as a probe for blood oxygenation, Magn. Reson. Med. 2000; 491-496. Therefore, it can be assumed that the observed "tissue" signal, $S_t$, in the present investigation is the sum of $S_{tissue}$ and $S_{plasma}$ as expressed below:

"tissue" signal $S_t(t) = S_{tissue}(t) + S_{plasma}(t) \equiv S_{t0} + S_{t1}t$   Equation (20A)

"blood" signal $S_b(t) = S_{RBC}(t) \equiv S_{b0} + S_{b1}t$   Equation (20B)

$S_{t0} = \alpha \lambda_T A_a L_t + \alpha \lambda_{pl} A_a L_c (1 - H)$   Equation (20C)

$S_{t1} = (1 - H) F \alpha \lambda_{pl}$   Equation (20D)

$S_{b0} = \alpha \lambda_{RBC} A_a L_c H$   Equation (20E)

$S_{b1} = HF\alpha \lambda_{RBC}$   Equation (20F)

The parameters $S_{t0}$, $S_{t1}$, $S_{b0}$ and $S_{b1}$, represent the intercept and slope of the asymptotes of the tissue and blood signals (signal build-up or uptake curves) as shown in FIG. 10. FIG. 10 illustrates the signal build-up curves for each of the alveolar gas signal, the tissue signal, and the blood or capillary signal, which correspond to the NMR-signal strength or intensity of the polarized $^{129}$Xe over time. The asymptotic slopes and intercepts can be used to calculate selected parameters such as tissue thickness, capillary thickness, perfusion, mean transit time and alveolar radius. These parameters can be used for calculation of the tissue thickness $L_t$ and the capillary thickness $L_c$ as follows:

$$L_t = \frac{S_{t0} H \lambda_{RBC} - S_{b0}(1-H)\lambda_{pl}}{S_{t0} H \lambda_{RBC} + S_{b0}(\lambda_T - (1-H)\lambda_{pl})} L$$   Equation (21A)

$$L_c = \frac{S_{b0}\lambda_T}{S_{t0} H \lambda_{RBC} + S_{b0}(\lambda_T - (1-H)\lambda_{pl})} L$$   Equation (21B)

Where "L" can be obtained based on data obtained from the portion of the curve representing the uptake time constant such as defined in Equation 18.

Several important physiological quantities can be calculated from one or more of Equations 20A-20F. For example, the hematocrit, H, the lung perfusion, $\dot{Q}$, given by $F/(V_t+V_c)$ and the mean transit time, $M_{TT}$, given by $V_c/F$. The following expressions can be used to calculate these parameters.

$$H = \frac{S_{b1}\lambda_{pl}}{S_{t1}\lambda_{RBC} + S_{b1}\lambda_{pl}}$$   Equation (22A)

$$\dot{Q} = \frac{S_{b1}\lambda_T}{S_{b0}(\lambda_T - (1-H)\lambda_{pl}) + S_{t0}\lambda_{RBC}H}$$   Equation (22B)

$$M_{TT} = \frac{S_{b0}}{S_{b1}}$$   Equation (22C)

The relative blood volume, rBV, given by $M_{TT}\dot{Q}$ can therefore be expressed as $L_c/L$. Additionally, with the simplification that the tissue-blood partition coefficient is sufficiently close to 1, the ratio between alveolar volume, $V_a$ and the effective total volume, $V_a+\lambda_T(V_t+V_c)$, equals the ratio $S_{a0}/S_a(0)$, where $S_a(0)$ is the gas signal at time t=0 and $S_{a0}$ is the intercept of the asymptote to the gas signal. Hence, the alveolar volume can be calculated:

$$V_a = \frac{\lambda_T S_{a0}(V_t + V_c)}{S_a(0) - S_{a0}}$$   Equation (23)

Using the relationships $V_a = 4/3\pi r_a^3$, and $(V_t+V_c) A_a L$, the alveolar radius can be calculated using the following expression:

$$r_a = \frac{3\lambda_T S_{a0}}{S_a(0) - S_{a0}} L$$   Equation (24)

where L is known from Equation 18.

Experimental Methods

Polarization and Administration of 129Xe $^{129}$Xe was polarized using a prototype commercial polarizer (IGI. 9800, Amersham Health, Durham, N.C.). A gas mixture of 1% natural abundance $^{129}$Xe, 10% N2 and 89% $^4$He flowed at a rate of 0.9 l/min through an optical cell where the $^{129}$Xe spins were polarized via spin exchange with optically pumped Rb vapor. The polarized $^{129}$Xe was accumulated for 30 min and frozen at liquid nitrogen temperature. After thawing, the polarized $^{129}$Xe was collected in a bag (volume 300 ml, Tedlar®, Jensen Inert, Coral Springs, Fla.) at 1 atm pressure. The polarization level in the bag was measured using a stand-alone calibration station (Amersham Health, Durham, N.C.) before and after each experiment in order to calculate the T1 relaxation time within the bag during the experiment. The initial polarization level in the bag was measured at about 8%-12%.

The bag containing the polarized $^{129}$Xe was connected to an in-house-built, computer-controlled respirator. Via a switch valve, the respirator was capable of administering either air or polarized $^{129}$Xe to the animal. The bag was placed within a rigid cylinder and positioned at about 0.5 m outside the magnet. To expel the polarized gas, the cylinder was pressurized with nitrogen. The computer control also served to trigger the MR sequence, i.e., to synchronize gas delivery and data acquisition. The reproducibility of administered gas volumes was tested in separate experiments and was better than 2% (data not shown).

Animal Preparation

All experiments were approved by the local ethical committee (Malmö/Lunds djurförsöksetiska nämnd; appl. no. M4-01). Ten Wistar rats (male, 250-360 g; breeder: M&B, Ry, Denmark) were instilled intratracheally with 1.0 mg LPS (Sigma Chemical, St. Louis, Mo.) per animal, dissolved in 0.1 ml 0.9% saline. The instillation was performed 48 hours prior to the NMR examination. A group of ten untreated Wistar rats (male, 270-340 g) served as controls. The animals were anesthetized subcutaneously with a mixture of fluanisone/fentanyl (Hypnorm™, Janssen Animal Health, Saunderton, England) and midazolam (Dormicum®, Hoffman-La Roche AG, Basel, Switzerland). The left jugular vein and the right carotid artery were catheterized for intravenous administration of anesthesia and a neuromuscular blocking agent (pancuronium, Pavulon®, Organon Teknika, Boxtel, the Netherlands), and for measurement of arterial blood pressure. After tracheal intubation, the animals were placed in the MR scanner in supine position and ventilated by the respirator mentioned above. During the experiment, body temperature, blood pressure, inspiratory pressure and tidal volume were monitored continuously. The breathing rate was set to 40 breaths/minute and the tidal volume to 1.0 ml per 100 g body weight. Inspiration and expiration times were 0.5 s.

Xenon Spectroscopy

All experiments were performed on a 2.35 T scanner (BioSpec 24/30, Bruker Biospin, Ettlingen, Germany) using a double-tuned birdcage RF coil (Bruker Biospin) with 72 mm diameter and 110 mm length, operating at the Larmor frequencies of 1 H (100.1 MHz) and 129Xe (27.7 MHz). The acquisition schematic of ventilator operation and NMR data acquisition is shown in FIG. 11. As shown, the repetition cycle included eighteen air-breaths followed by three xenon breaths. After the last xenon inspiration, a 90° RF pulse was applied to destroy the signal in tissue and blood, followed by a second 90° RF pulse generating a FID from the xenon in tissue and blood. The interpulse delay $\Delta(n)$ was increased between successive repetitions.

Thus, a ventilator cycle consisted of 18 air breaths followed by three xenon breaths. The breathing was interrupted after the third xenon inspiration for a 7 s breathhold and a trigger pulse was sent from the ventilator to the NMR scanner in order to initiate data accumulation. A 90° RF excitation with center frequency between the tissue and blood xenon resonances was applied in order to remove all signal arising from xenon in tissue and blood, while preserving the hyperpolarization in the alveolar gas. After a delay $\Delta(n)$, a second 90° RF excitation followed, generating a FID signal from xenon having diffused from the alveoli to tissue and blood during the delay $\Delta(n)$. During the breath-hold period, the RF pulses and data accumulation were repeated 12 times in an averaging loop, before continuing with the next ventilator cycle. The ventilator cycle was repeated 12 times (n=1 ... 12) with increasing values of the delay $\Delta(n)$ (15, 20, 30, 40, 60, 90, 120, 150, 200, 300, 400 and 500 ms, respectively), resulting in a total experiment duration of 8 minutes.

Before each experiment, the flip angle of the RF pulses was adjusted to 90° by applying a train of 4 RF pulses with center frequency at the gas resonance. The adjustment was repeated and the amplitude of the RF pulses fine-tuned until no FID signal could be detected after pulses 2-4. With the center frequency between the tissue and blood resonances, the duration of the rectangular RF pulses was adjusted to give minimum excitation of the alveolar gas, i.e., the first zero crossing of the sinc-shaped frequency response of the RF pulse was adjusted to correspond to the gas resonance. The excitation of the gas signal was measured in a separate experiment and was found to be approximately 7° (data not shown).

Parametric Analysis

The data analysis was made with software implemented in MATLAB (MathWorks, Natick, Mass.). After zero and first order phase corrections, Lorentzian shape functions were fitted to the gas, tissue and blood peaks of each spectrum. The peak amplitudes of the fitted functions were corrected for the T1 relaxation decay of the polarized $^{129}$Xe in the reservoir during the course of the experiment. Because the repetition time within the averaging loop increased with increasing delay $\Delta(n)$, the peak amplitudes were additionally corrected for the T1 relaxation in the lung during the data accumulation, using a fixed T1 relaxation of 30 s in the gas phase. See Albert et al., *Biological magnetic resonance imaging using laser polarized $^{129}$Xe*, Nature, 1994: 370: 199-201. The functions expressed below were fitted to the amplitudes of the gas, tissue and blood peaks, as function of the delay.

$$S_g(\Delta) = S_{0,g} \exp(-\Delta/\tau_g) + S_{1,g} \text{(gas peak)} \quad \text{Equation (25A)}$$

$$S(\Delta) = S_0(1 - \exp(-\Delta/\tau_1)) + S_1 \Delta \text{(tissue and blood peaks)} \quad \text{Equation (25B)}$$

The resulting time constant $\tau_1$ from the tissue peak was used for calculation of the total diffusion length "L" (Equation 18). The intercept, $S_0$, and slope, $S_1$, from the tissue and blood peaks were used to calculate $L_t$, $L_c$, $\dot{Q}$ and $M_{TT}$, according to Equations 21A, 21B and 22A-22C. These calculations were performed using Ostwald solubility coefficients of $\lambda_T = 0.1$, $\lambda_{pl} = 0.09$, $\lambda_{RBC} = 0.2$ and a fixed hematocrit H=0.45. The Ostwald solubility coefficients were obtained from work described by other researchers. See Ladefoged et al., *Solubility of xenon-133 at 37° C. in water, aline olive oil, liquid paraffin, solutions of albumin, and blood*, Phys Med Biol 1967; 19: 72-78; Hellberg et al., *Red cell trapping after ischemia and long-term kidney damage. Influence of hematocrit*, Kidney Int, 1990; 37: 1240-1247; and Penney et al., *Heart and lung hypertrophy, changes in blood volume, hematocrit and plasma rennin activity in rats chronically exposed to increasing carbon monoxide concentrations*, J App Toxicol, 1988; 8: 171-178. The contents of these documents are hereby incorporated by reference herein.

Additionally, the alveolar radius was estimated using Equation 24 and the relative blood volume was calculated as rBV=Lc/L. p-values, comparing the LPS-treated group with the controls, were calculated using the Student's t-test (double-sided, unequal variance).

Results

Xe Spectroscopy

In all spectra, gas, tissue, and blood compartment signals were clearly visible with the tissue compartment signal SNR ranging from 20 (shortest delay) to 80 (longest delay). The tissue and blood signals were well separated at 198 ppm and 212 ppm respectively, with amplitudes approximately half of the gas signal amplitude. The T1 relaxation of xenon in the reservoir was in the range 60-80 min, corresponding to a maximum signal decay of about 0.9 during the experiment. A representative set of spectra is shown in FIG. 12 as a stacked plot. The representative spectra data illustrated in FIG. 12 were obtained from a naïve rat. The 12 spectra shown correspond to increasing time delays $\Delta$, during which the xenon diffuses from the alveoli to the capillaries. The decreasing amplitude of the alveolar gas signal due to the uptake of xenon is observable.

Parametric Analysis

The fit of the functions given by Equations 25A and 25B to the tissue, blood, and gas amplitudes yielded $R^2$ values of 0.98±0.02 (tissue), 0.99±0.02 (blood) and 0.95±0.04 (gas) in the control group (mean±SD). In the LPS-treated group, the corresponding values were 0.99±0.02, 0.97±0.09 and 0.90±0.09, respectively. A representative example of the fit is presented in FIGS. 13A and 13B. The peak amplitudes of the signal in the tissue compartment (FIG. 13A) and blood compartment (FIG. 13B) in a representative control animal and LPS-treated animal, are shown as a function of delay time $\Delta$ (ms). The associated data points in the line are illustrated by circles, with the LPS treated animal being the solid or filled circle and the control animal being non-filled. The solid and dashed or broken lines illustrate the fit of Equation 25B to the data. In FIGS. 13A and 13B, the amplitude of the LPS-treated animal has been scaled to give equal amplitude as the control at 200 ms delay time.

In the control group, the time constant $\tau_1$ was determined to be 30±3 ms using the tissue signal and to 26±5 ms using the blood signal. The ratio of the tissue and blood time constants was 1.17±0.23. In the LPS-treated group, the corresponding time constants were 41±6 ms (tissue) and 33±10 ms (blood) with ratio 1.28±0.22. Due to its lower standard deviation, the tissue time constant was selected for calculation of the total diffusion length, L. The time constant of the gas signal, $\tau_g$, was 257±137 ms in the control group and 195±104 ms in the LPS-treated group.

Significant differences in total diffusion length (L) and tissue thickness ($L_t$) were found between the control group and the LPS-treated group, whereas no significant difference in capillary diffusion length (Lc), perfusion ($\dot{Q}$), mean transit time ($M_{TT}$), relative blood volume (rBV) or alveolar radius ($r_a$) could be detected. Table 2 provides a summary of the numerical values for these parameters.

TABLE 2

Summary of the calculated parameters using the diffsion model.
Values are given as mean ± SD.

| Parameter | Control group | LPS group | p-value Control vs. LPS |
|---|---|---|---|
| Total diffusion length (L = $L_t$ + $L_c$), μm | 8.6 ± 0.5 | 10.0 ± 0.8 | 0.00013 |
| Tissue thickness ($L_t$), μm | 4.9 ± 0.9 | 6.4 ± 1.2 | 0.0080 |
| Blood thickness ($L_c$), μm | 3.6 ± 0.8 | 3.6 ± 1.3 | 0.95 |
| Perfusion (Q), (ml s$^{-1}$/ml) | 1.5 ± 0.3 | 1.3 ± 0.2 | 0.13 |
| Mean transit time ($M_{TT}$), s | 0.30 ± 0.11 | 0.29 ± 0.10 | 0.68 |
| Relative blood volume (rBV) | 0.43 ± 0.10 | 0.36 ± 0.12 | 0.19 |
| Alveolar radius ($r_a$), μm | 8.7 ± 3.2 | 8.5 ± 2.1 | 0.89 |

Discussion

The pulmonary tissue compartment in the diffusion model described above is composed of the alveolar liquid lining, the epithelium, a very thin interstitial space, and the endothelium. The thickness of the blood-gas barrier is known to vary around the capillaries. However, as the polarized $^{129}$Xe NMR measurement was not spatially resolved in the investigation described herein, the tissue thickness calculated from the xenon uptake time-constant should be regarded as an average value for the alveolar-capillary membrane thickness, including tissue separating neighboring capillaries and perivascular interstitial space. Measurement of the average membrane thickness agrees well with the actual dimensions of the membrane, which has been measured to 5-6 μm in the rat using microscopic methods as well as with NMR techniques. See Tanaka et al., *Maturational changes in extracellular matrix and lung tissue mechanics.*, J Appl Physiol, 2001; 91; 2314-2321; and Albertine, K. H., *Structural organization and quantitative morphology of the lung*, 1 ed., In: Cutillo AG (Editor). Application of magnetic resonance to the study of the lung, NY, Futura; 1996, p. 73-114. The contents of these documents are hereby incorporated by reference as if recited in full herein.

The membrane thickness is an important indicator of the diffusing capacity of the lung, since the diffusing capacity is inversely proportional to this thickness. See Roughton et al., *Relative importance of diffusion and chemical reaction rates in determining rate of exchange of gases in the human lung, with special reference to true diffusing capacity of pulmonary membrane and volume of blood in the lung capillaries*, J Appl Physiol, 1957; 11:290-302, the contents of which is hereby incorporated by reference as if recited in full herein. A reduced diffusing capacity caused by loss of alveolar surface area will however not be revealed by the uptake time constant. The uptake time constant is inversely proportional to the gas diffusion coefficient. Since the diffusion coefficients are similar for xenon (1·10$^{-9}$ m$^2$/s) and for oxygen (1.7·10$^{-9}$ m$^2$/s), one can expect that the dynamics of the xenon uptake is not much different from that of oxygen. For the former see Wolber et al., supra and for the latter see Sharan et al., *finite-element analysis of oxygen transport in the systemic capillaries*, IMA J Math Appl Med Biol 1991; 8: 107-123. The contents of each of these documents are hereby incorporated by reference as if recited in full herein.

Although the model is a simplification of the actual lung morphology, the experimental results agree in several respects with the predictions from the theoretical analysis. The model uses equal time constants for the initial signal build-up in both tissue and blood, which agrees with the measured "tissue" and "blood" time constants having a ratio close to unity. A statistically significant difference in the Xe uptake time constant was observed—and hence in the membrane thickness—between the control animals and the LPS-treated group of animals. The difference in length was related to the "tissue" thickness only, whereas the "capillary" thickness was substantially equal in both groups. This finding is consistent with the acute inflammatory lung injury caused by the LPS, which is expected to increase the alveolar wall thickness, but not to alter the capillary blood volume within the lung.

In addition, perfusion can be measured using the xenon uptake method. The slopes and intercepts of the dissolved-phase $^{129}$Xe signals after the initial exponential buildup are used for calculation of the quantities mean transit time, perfusion, and relative blood volume.

Other past studies on rats using non-NMR methods have reported a total pulmonary blood flow of approximately 2 ml/s, a total capillary volume of approximately 1 ml, and a total alveolar wall volume of 1 ml. From this data, the perfusion can be calculated to 1 ml·s$^{-1}$/ml, the mean transit time to 0.5 s and the relative blood volume to 0.5, which are in fair agreement with the corresponding values obtained in the present study. The mean transit time did not differ between the control group and the LPS group. This observation further supports the assumption that the total blood volume, and thus the "blood thickness", remained unaffected by the LPS treatment. The mean transit time is one order of magnitude larger than the observed uptake time constant (30 ms in the control group, 41 ms in the LPS group). Consequently, the xenon concentrations in blood and tissue are well equilibrated before the blood leaves the alveolar capillary. The ratio between the uptake time constant and the mean transit time can be used to indicate whether the gas exchange is perfusion or diffusion limited. The calculated lung perfusion and relative blood volume differed between the groups, although not significantly (p=0.13 and p=0.19, respectively). The tendency for reduced perfusion and relative blood volume in the LPS-treated group is consistent with an increased total volume (tissue plus blood) in the treated group, at unaltered blood flow.

Among the calculated model parameters, the total diffusing thickness, L, is obtained directly from the uptake time constant, $\tau_1$, in contrast to the other parameters, which depend on the slope and/or intercept of the NMR signal uptake curves.

The present study averaged several accumulations in order to obtain spectra with sufficient SNR, resulting in accumulation times of several seconds for the longest delays. This may be less than optimal, since the alveolar gas signal decreases after inspiration due to the T1 relaxation in the lung and the transport of xenon to the capillary. The T1 relaxation was compensated for, whereas a compensation for the signal drop caused by removal of xenon from the alveolus could not be done. Therefore, the slope and intercept values were more difficult to determine accurately than the uptake time constant, making the parameter L the most reliable measure of pathological condition.

In addition, it is noted that the inverse of the uptake time constant, $\tau_1^{-1}$, can act as a sensitive indicator of alveolar membrane thickening, as it is a quadratic function in L.

The measurement of the alveolar radius in this study (~8 µm) resulted in an underestimation compared to the expected value of about 35 µm (as described by Altman et al., *Respiration and circulation*, Bethesda: Federation of American societies for experimental biology; 1971, p. 930). Of the measured signals during the experiment, the gas signal was the most difficult to quantify, with a more fluctuating amplitude than the tissue and blood peaks. The fluctuating signal amplitude caused difficulties to obtain reproducible results from this peak, making it more difficult to obtain reliable measurements of the alveolar radius.

In principle, the polarized $^{129}$Xe uptake study provides the same information as the CO transfer test, as both methods assess the membrane-related and the vascular aspects of lung function. The quantity obtained from the CO function test, DLCO, is a function of lung surface area, membrane thickness, and blood volume. However, the latter physiological quantities are not easily obtained from the CO transfer test. In contrast, the $^{129}$Xe method allows direct quantification of the most important physiological parameters from the initial uptake dynamics of the gas. With some increase in $^{129}$Xe polarization and a greater total volume of hyperpolarized gas available for the study, it may also be possible to differentiate Xe uptake in several regions of interest within the lungs by means of localized NMR spectroscopy. Another extension of the present study would be a complementary quantitative method for measuring lung ventilation using hyperpolarized $^{129}$Xe, which would allow a comprehensive characterization of lung function with a single diagnostic modality.

In summary, the mathematical diffusion model allows the quantification of lung physiological parameters from the uptake dynamics of hyperpolarized $^{129}$Xe, as measured by data obtained from NMR-spectroscopy. The relationship between the uptake time constant and the total diffusion length across the respiratory membrane allows NMR data to quantify this length. Furthermore, quantitative information about pulmonary perfusion can be extracted from the polarized $^{129}$Xe NMR data set. Thus, two main components of lung function—membrane diffusing capacity and pulmonary perfusion—can be obtained in a single study or clinical session using the same or common dose(s) of $^{129}$Xe. The proposed analysis operations were employed for comparison of a control group of rats versus a group of LPS-treated rats. A statistically significant increase in the diffusion length, related to a thickening of the alveolar wall was measured in the latter group, whereas no significant differences in perfusion related parameters were observed. The proposed operations are able to distinguish alterations related to diffusive capacity from alterations of pulmonary perfusion.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

The invention claimed is:

1. An in vivo method for evaluating whether a subject has a respiratory disorder, or a cardiopulmonary disorder, comprising:
   delivering polarized $^{129}$Xe in vivo to a subject such that the polarized $^{129}$Xe travels across the alveolar-capillary membrane to be taken up in the blood across the membrane, the polarized gas in the blood having a polarized $^{129}$Xe NMR chemical shift signal frequency;
   destroying the polarization of the polarized $^{129}$Xe in the blood and the membrane;
   obtaining an NMR spectroscopic signal of the polarized gas in the subject over time at the blood and/or tissue resonant frequency to generate at least one dynamic data set to generate at least one NMR $^{129}$Xe uptake curve at least one chemical shift frequency of interest of signal strength values over time; and
   evaluating the NMR derived dynamic data set to assess whether the subject has a respiratory or cardiopulmonary disorder.

2. A method according to claim 1, wherein the subject is evaluated for chronic heart failure.

3. A method according to claim 1, further comprising:
   calculating a time constant associated with the time it takes the polarized gas to travel across the membrane and then enter the blood after said destroying step; and
   determining a diffusion thickness based on data provided by said obtaining and calculating steps.

4. A method according to claim 3, wherein the step of obtaining comprises obtaining a plurality of signal data points over a time which is greater than about twice the time constant.

5. A method according to claim 3, wherein said obtaining step is carried out when the subject is at rest and then repeated while the subject is exposed to conditions of actual or chemically induced exercise, and wherein said method further comprises comparing the time constants associate therewith to thereby assess the function of the alveolar-capillary membrane.

6. A method according to claim 4, further comprising calculating asymptotes and intercepts of the NMR $^{129}$Xe signal uptake curves from the NMR data and determining the membrane thickness, wherein the membranes have a thickness in the range of between about 1 micron to about 100 microns.

7. A method according to claim 1, wherein the obtaining step is carried out a plurality of times, including at least once while the subject is at rest and at least once when the subject is under or just after actual or simulated physical activity when the heart rate is elevated.

8. A method according to claim 1, wherein the obtaining step is performed after a therapeutic agent is administered to the subject to evaluate the efficacy in treating the disorder or to evaluate its impact on the thickness of the alveolar-capillary membrane.

9. A method according to claim 8, wherein the obtaining step is carried out both before and after the administration of the therapeutic to the subject.

10. A method according to claim 1, wherein the evaluating step comprises evaluating at least one of thickness of the alveolar-capillary membrane, perfusion in the pulmonary blood, and ejection fraction, based on said obtaining step.

11. A method according to claim 1, further comprising providing a predetermined diffusion model of alveolar gas exchange employing an alveolar gas compartment, a tissue compartment, and a capillary compartment; and
calculating a plurality of selected bioparameters related to lung function and/or physiology using NMR-derived data associated with $^{129}$Xe uptake curves and the predetermined diffusion model.

12. A method according to claim 11, further comprising computing a total diffusion length "L" associated with the combined tissue compartment thickness and the capillary compartment thickness by the equation:

$$L \approx \frac{\pi}{2}\sqrt{D\tau_1}$$

where D is a diffusion coefficient of xenon in the tissue and/or capillary and $\Sigma_1$ is an uptake time constant associated with an initial portion of the uptake curve of the NMR signal of the polarized $^{129}$Xe in the combined tissue and capillary compartment.

13. A method according to claim 11, wherein the calculating step is carried out by combining the tissue and capillary compartments into a single compartment using a common $^{129}$Xe concentration value.

14. A method according to claim 11, further comprising:
defining equations representing the NMR signals associated with each of tissue, plasma and red blood cells using a respective Ostwald solubility coefficient for each compartment; and
computing at least one of a time constant, intercept and slope of an asymptote derived from the signal build up curve of polarized $^{129}$Xe associated with the tissue and capillary compartments derived from the NMR dynamic data set to determine a plurality of selected parameters related to perfusion and/or diffusion.

15. A method according to claim 14, wherein the computing step computes the intercept and slope asymptote values for both the tissue uptake curve and the blood compartment uptake curve based on the NMR data.

16. A method according to claim 14, further comprising evaluating the dynamic NMR data set to determine the NMR uptake curve signal of the $^{129}$Xe associated with the tissue, plasma and red blood cells.

17. A method according to claim 11, further comprising concurrently assessing diffusing capacity and pulmonary perfusion using the $^{129}$Xe NMR data set.

18. A method according to claim 11, wherein the concurrently determined parameters include at least two of: tissue thickness, capillary thickness, perfusion, mean transit time and alveolar radius.

19. A method according to claim 18, wherein the parameters comprise at least two of hematocrit, perfusion, and mean transit time.

20. A method according to claim 18, wherein the parameters comprise pulmonary perfusion.

21. A method according to claim 11, further comprising determining a hematocrit value based on the $^{129}$Xe-NMR data set.

22. A method according to claim 11, wherein the parameters include at least two of the alveolar radius, the alveolar volume, and the relative blood volume based on the $^{129}$Xe NMR data set.

23. A method according to claim 1, further comprising evaluating the subject for indications of a drug-induced lung disorder and/or injury.

24. A method according to claim 11, further comprising evaluating the subject for an environmentally induced lung injury based on the NMR-derived dynamic data set.

25. A method according to claim 11, further comprising evaluating the subject for at least one of pulmonary inflammation, pulmonary edema, pulmonary hypertension, pneumonitis, and pulmonary fibrosis based on the $^{129}$Xe NMR data set.

26. A method according to claim 1, further comprising monitoring the subject for indications of a transplant rejection based on the $^{129}$Xe NMR data set.

27. An in vivo method for evaluating a subject for chronic heart failure comprising:
(a) delivering polarized $^{129}$Xe in vivo to a subject such that the polarized $^{129}$Xe moves across the alveolar-capillary membrane to be taken up in the blood across the membrane, the polarized gas in the blood having a corresponding polarized gas NMR chemical shift signal frequency;
(b) destroying the polarization of the polarized $^{129}$Xe in the blood and the membrane;
(c) obtaining an NMR spectroscopic signal of the polarized $^{129}$Xe in the subject over time at the blood chemical shift frequency to generate at least one dynamic data set of the NMR spectroscopic signal strength over time;
(d) evaluating the dynamic data; and
(e) determining whether the subject has chronic heart failure based on the obtaining and evaluating steps.

* * * * *